(12) United States Patent
Nema et al.

(10) Patent No.: US 9,518,960 B2
(45) Date of Patent: Dec. 13, 2016

(54) SYSTEM AND METHOD FOR RAPID ANALYSIS OF POLYCYCLIC AROMATIC HYDROCARBONS

(71) Applicant: Waters Technologies Corporation, Milford, MA (US)

(72) Inventors: Tarang Nema, Singapore (SG); Melvin Gay, Singapore (SG); Mark Ritchie, Singapore (SG)

(73) Assignee: Waters Technologies Corporation, Milford, MA (US)

( * ) Notice: Subject to any disclaimer, the term of this patent is extended or adjusted under 35 U.S.C. 154(b) by 251 days.

(21) Appl. No.: 14/503,998

(22) Filed: Oct. 1, 2014

(65) Prior Publication Data

US 2015/0089997 A1    Apr. 2, 2015

Related U.S. Application Data

(60) Provisional application No. 61/886,044, filed on Oct. 2, 2013.

(51) Int. Cl.
*B01J 20/28*        (2006.01)
*G01N 30/52*        (2006.01)
*G01N 30/06*        (2006.01)
*G01N 30/88*        (2006.01)
*B01J 20/287*       (2006.01)

(Continued)

(52) U.S. Cl.
CPC ............. *G01N 30/06* (2013.01); *B01J 20/287* (2013.01); *B01J 20/288* (2013.01); *G01N 30/52* (2013.01); *G01N 30/88* (2013.01); *G01N 30/68* (2013.01); *G01N 30/72* (2013.01); *G01N 30/74* (2013.01); *G01N 2030/525* (2013.01); *G01N 2030/8854* (2013.01)

(58) Field of Classification Search
CPC ... B01D 15/40; B01D 2253/202; B01D 15/26; B01D 2253/106; B01D 2253/25; B01D 2258/06; B01D 53/02; B01J 20/28057; B01J 20/28061; B01J 20/28069; B01J 20/28073; B01J 20/28083; B01J 20/28085; B01J 20/103; B01J 20/16; B01J 20/28004; B01J 20/28016; B01J 20/28064; B01J 20/28066; B01J 20/28071; B01J 20/28076; B01J 20/28078; B01J 20/28059; G01N 30/02; G01N 30/06; G01N 2030/143; G01N 2030/525; G01N 2030/8854
See application file for complete search history.

(56) References Cited

U.S. PATENT DOCUMENTS 4,017,528 A * 4/1977 Unger ................... C08G 77/02
502/150
4,415,631 A * 11/1983 Schutijser ............ C08F 292/00
210/198.2

(Continued)

OTHER PUBLICATIONS

Gilgenast et al., "Sample preparation procedure for the determination of polycyclic aromatic hydrocarbons in petroleum vacuum residue and bitumen", Anal Bioanal Chem (2011) 401:1059-1069, Jun. 7, 2011.*

*Primary Examiner* — David A Rogers
(74) *Attorney, Agent, or Firm* — McCarter & English, LLP; Deborah M. Vernon; Michael J. DeGrazia

(57) ABSTRACT

The subject technology is directed to a $CO_2$-based system and method for rapid determination of the levels and/or the presence or absence of polycyclic aromatic hydrocarbons (PAHs).

29 Claims, 8 Drawing Sheets

(51) Int. Cl.
  *B01J 20/288* (2006.01)
  *G01N 30/72* (2006.01)
  *G01N 30/68* (2006.01)
  *G01N 30/74* (2006.01)

(56) References Cited

U.S. PATENT DOCUMENTS

| | | | | |
|---|---|---|---|---|
| 4,767,670 | A * | 8/1988 | Cox | B01D 15/325 |
| | | | | 210/656 |
| 5,198,115 | A * | 3/1993 | Stalling | G01N 25/14 |
| | | | | 210/137 |
| 5,374,755 | A * | 12/1994 | Neue | B01D 15/325 |
| | | | | 210/198.2 |
| 6,528,167 | B2 * | 3/2003 | O'Gara | B01J 20/103 |
| | | | | 428/402 |
| 6,686,035 | B2 * | 2/2004 | Jiang | B01J 20/103 |
| | | | | 210/198.2 |
| 7,125,488 | B2 * | 10/2006 | Li | B01J 20/3227 |
| | | | | 210/198.2 |
| 7,179,364 | B2 * | 2/2007 | O'Rear | C10G 2/30 |
| | | | | 208/15 |
| 2006/0207923 | A1 * | 9/2006 | Li | B01J 20/3227 |
| | | | | 210/198.2 |
| 2007/0090052 | A1 * | 4/2007 | Broske | B01J 20/286 |
| | | | | 210/656 |
| 2007/0135304 | A1 * | 6/2007 | Walter | B01J 20/28033 |
| | | | | 502/402 |
| 2007/0189944 | A1 * | 8/2007 | Kirkland | B01J 20/28004 |
| | | | | 423/118.1 |
| 2008/0203027 | A1 * | 8/2008 | Liu | B01J 20/286 |
| | | | | 210/656 |
| 2008/0264254 | A1 * | 10/2008 | Song | B01D 53/02 |
| | | | | 95/116 |
| 2009/0209722 | A1 * | 8/2009 | Jiang | B01J 20/26 |
| | | | | 528/25 |
| 2011/0049056 | A1 * | 3/2011 | Wyndham | B01D 15/08 |
| | | | | 210/656 |
| 2012/0055860 | A1 * | 3/2012 | Wyndham | B01J 20/286 |
| | | | | 210/198.3 |
| 2012/0273404 | A1 * | 11/2012 | Wyndham | B01J 20/286 |
| | | | | 210/198.2 |
| 2013/0133516 | A1 * | 5/2013 | Okano | B01D 15/40 |
| | | | | 95/88 |
| 2014/0319057 | A1 * | 10/2014 | Brousmiche | B01D 15/26 |
| | | | | 210/656 |
| 2015/0089997 | A1 * | 4/2015 | Nema | G01N 30/52 |
| | | | | 73/23.4 |

* cited by examiner

SYSTEM AND METHOD FOR RAPID ANALYSIS OF POLYCYCLIC AROMATIC HYDROCARBONS

RELATED APPLICATIONS

This application claims the benefit of U.S. Provisional Application No. 61/886,044, filed Oct. 2, 2013, the entire content of which are incorporated herein by reference.

FIELD

The subject technology relates to $CO_2$-based chromatography; in particular, the subject technology relates to a $CO_2$-based chromatography system ("$CO_2$-based system") and method for analysis of polycyclic aromatic hydrocarbons (PAHs).

BACKGROUND

Polycyclic aromatic hydrocarbons (PAHs), also known as poly-aromatic hydrocarbons or polynuclear aromatic hydrocarbons, are potent atmospheric pollutants that consist of fused aromatic rings and do not contain heteroatoms or carry substituents. Naphthalene is the simplest example of a PAH. PAHs occur in oil, coal, and tar deposits, and are generally produced as byproducts of fuel burning (whether fossil fuel or biomass) or incomplete combustion or pyrolysis of organic matter. Due to the great number of applications of combustion in our daily lives (e.g., heating, cooking, fossil fuel burning, cigarette smoking and etc., PAHs are formed in great abundance. In addition, since each of these combustion processes occurs at various temperatures and under various environmental conditions, different PAHs are formed. Emitted PAHs generally absorb on the surface of soot particles, thus allowing the dispersion of these compounds throughout the environment. As a pollutant, PAHs are of concern because a number of them have been identified as carcinogenic, mutagenic, and teratogenic.

Currently, there are twenty-four PAHs that have been identified as being hazardous to human health. See Table 1. The EU Scientific Committee for Food (SCF), the European Union (EU), and the US Environmental Protection Agency (EPA) recommend a frequent monitoring of these twenty-four PAHs. This list is expected to grow longer as more PAHs with potentially toxic properties are identified. Therefore, there is a need for an efficient monitoring of PAHs in the environment and in almost anything (e.g., food, beverages, packaging materials, medical devices, etc.) that may increase the risk of human exposure to these compounds.

TABLE 1

Names and structures of frequently monitored PAHs. (source: Polycyclic Aromatic Hydrocarbons (PAHs) Factsheet, 3rd edition, European Comission, Joint Research Centre; Institute for Reference Materials and Measurements; European Union 2010)

| List | Common Name | Structure |
|---|---|---|
| EPA, SCF, EU | Benzo[a] pyrene | 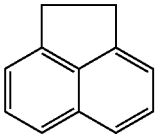 [SMILES: c1cc2c3c(cccc3c1)CC2] |

TABLE 1-continued

Names and structures of frequently monitored PAHs. (source: Polycyclic Aromatic Hydrocarbons (PAHs) Factsheet, 3rd edition, European Comission, Joint Research Centre; Institute for Reference Materials and Measurements; European Union 2010)

| List | Common Name | Structure |
|---|---|---|
| EPA | Acenaphthene | 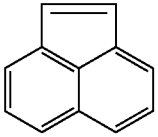 [SMILES: C1=Cc2cccc3cccc1c23] |
| EPA | Acenaphthylene | 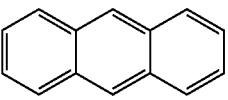 [SMILES: c1ccc2cc3ccccc3cc2c1] |
| EPA | Anthracene | 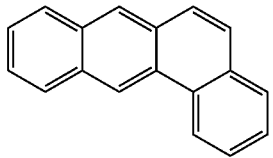 [SMILES: c1ccc2cc3c(ccc4ccccc43)cc2c1] |
| EPA, SCF, EU | Benzo[a] anthracene | 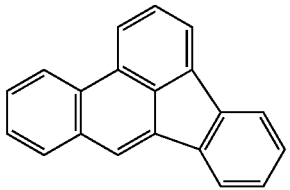 [SMILES: c1ccc2c(c1)-c1cccc3c1c-2cc1ccccc13] |
| EPA, SCF, EU | Benzo[b] fluoranthene | 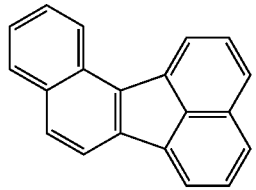 [SMILES: c1ccc2c3c(ccc2c1)-c1cccc2cccc-3c12] |
| SCF, EU | Benzo[j] fluoranthene | 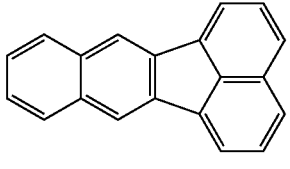 [SMILES: c1ccc2cc3c(cc2c1)-c1cccc2cccc-3c12] |
| EPA, SCF, EU | Benzo[k] fluoranthene | 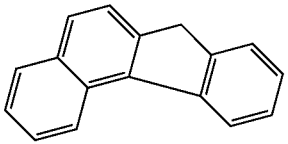 [SMILES: c1ccc2c(c1)Cc1ccc3ccccc3c1-2] |
| EU | Benzo[c]fluorene | 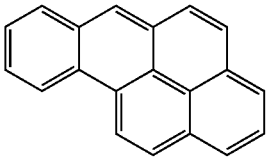 |

TABLE 1-continued

Names and structures of frequently monitored PAHs. (source: Polycyclic Aromatic Hydrocarbons (PAHs) Factsheet, 3rd edition, European Comission, Joint Research Centre; Institute for Reference Materials and Measurements; European Union 2010)

| List | Common Name | Structure |
|---|---|---|
| EPA, SCF, EU | Benzo[ghi]perylene | |
| EPA, SCF, EU | Chrysene | |
| SCF, EU | Cyclopenta[cd]pyrene | 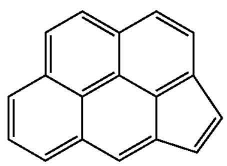 [SMILES: C1=Cc2cc3cccc4ccc5ccc1c2c5c43] |
| EPA, SCF, EU | Dibenzo[a,h]anthracene | |
| EU + SCF | Dibenzo[a,e]pyrene | |
| EU + SCF | Dibenzo[a,h]pyrene | |
| EU + SCF | Dibenzo[a,l]pyrene | |
| EU + SCF | Dibenzo[a,l]pyrene | |
| EPA | Fluoranthene | |
| EPA | Fluorene | |
| EPA, SCF, EU | Indeno[1,2,3-cd]pyrene | |
| EU + SCF | 5-Methylchrysene | |
| EPA | Naphthalene | |
| EPA | Phenanthrene | |
| EPA | Pyrene | |

Typical methods for analysis of PAHs include HPLC (high performance or pressure liquid chromatography) and GC (gas chromatography). However, there are shortcomings associated with each of these methods. For example, the GC methods only detect volatile compounds and non-volatile compounds require derivatization prior to a GC analysis, which is burdensome, expensive and time-consuming. In liquid chromatography methods, although no sample derivatization is required, the typical run time of a sample on an HPLC instrument is about 25 minutes; which has recently been reduced to about 10 minutes by using a UHPLC (ultrahigh performance or pressure chromatography) instrument. There are other disadvantages to using HPLC or UHPLC, one of which is their using of toxic organic solvents as mobile phase and generating toxic waste, which is expensive to purchase and dispose of.

The use of non-toxic Supercritical $CO_2$ (SC—$CO_2$) as an alternative to organic solvents as the mobile phase has resulted in the advent of supercritical fluid chromatography (SFC) which embraces many of the features of liquid and gas chromatography. Theoretically, SC—$CO_2$ provides a low viscosity mobile phase that achieves higher diffusion rates and enhanced mass transfer over the solvents used in HPLC. However, the current SFC instruments (which are mainly retooled HPLCs) and methods have many limitations including, for example, long sample run time, inaccurate or imprecise control over the mobile phase density and composition, inability to reliably deliver modifiers at low amounts (<5% of liquid $CO_2$), susceptibility to system pressure fluctuations and sample backflow, baseline noise, sample carryover, and lack of robustness, which prevent users from rapidly obtaining reproducible results.

Therefore, there still remains a need for a more improved chromatography system and method that can overcome the above limitations and allow for a rapid and robust analysis of PAHs.

SUMMARY

The subject technology is, in part, based on a discovery that many of the toxic PAHs can be conveniently and reproducibly analyzed in a short period of time (e.g., in less than about 5 minutes) by a $CO_2$-based chromatography method and system involving, inter alia, a stationary phase with particle sizes of about 0.5 to 3.5 μm in diameter, a $CO_2$ mobile phase with a pre-column dwell volume of about 75 μl to about 500 μl. The method and system of the subject technology generate high resolution chromatograms which allow for accurate detection and quantification of PAHs.

The subject technology is illustrated, for example, according to various aspects described below.

In another aspect, the subject technology relates to a method for detecting one or more polycyclic aromatic hydrocarbons (PAHs) in a sample by means of a $CO_2$-based chromatography analysis including: (1) providing a sample containing one or more PAHs for analysis; wherein the sample is prepared with, extracted or dissolved in a diluent comprising at least 60% organic solvent, with the proviso that the sample is analyzed without a solvent exchange step, i.e., the sample is not subject to a solvent exchange step once it is prepared or before analysis by the method of the subject technology; (2) applying the sample to a chromatography column with a solid stationary phase including inorganic or hybrid particles having a mean particle size of about 0.5 to about 3.5 microns, wherein said particles have a non-polar or polar/non-polar surface functionality, and wherein the particles retain said one or more PAHs; (3) eluting the one or more PAHs from the chromatography column by a mobile phase comprising a mixture of liquid $CO_2$ and a modifier to form one or more eluted PAHs, wherein the mobile phase has a pre-column dwell volume of about 75 μL to about 500 μL, wherein said dwell volume includes a space within a fluidic or tubular connection between a junction at which two or more mobile phase solvents (e.g., liquid $CO_2$ and a modifier) are mixed to the head of the column; and (4) detecting said one or more doted PAHs by a suitable detector or detecting device.

In an embodiment relating to this or any other aspects of the subject technology, the sample is not subject to a derivatization step because the method of the subject technology is sufficiently sensitive to detect minute amounts of PAHs in the sample and that no derivatization of the analytes is needed. In another related embodiment, the particles having a non-polar surface functionality include capped particles with non-polar surface modifiers including an alkyl group, alkenyl group, alkynyl group, aryl group, an alkyl or aryl group containing one or more embedded non-polar functionalities, or a mixture thereof. In another related embodiment, the particles having a polar/non-polar surface functionality include uncapped particles with free surface hydroxyl groups and non-polar surface modifiers including an alkyl group, alkenyl group, alkenyl group, aryl group, an alkyl or aryl group containing one or more embedded non-polar functionalities, or a mixture thereof. In another related embodiment, the particles have a mean particle size of about 0.5 to about 2 microns. In another related embodiment, the particles have a mean pore volume in the range of about 0.1 to about 2.5 cm/g. In another related embodiment, the particles have a mean pore diameter in the range of about 100 to about 1000 Angstroms. In another related embodiment, the inorganic particles include silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof. In another related embodiment, the hybrid particles include an inorganic portion and an organic portion. In another related embodiment, the inorganic portion of the hybrid particles includes silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof. In another related embodiment, the organic portion of the hybrid particles includes substituted or unsubstituted C1-C18 alkane, alkylene, alkenylene, alkynylene or arylene moiety bonded to one or more atoms of the inorganic portion. In another related embodiment, the organic portion of the hybrid particles includes substituted or unsubstituted C1-C18 alkylene, alkenylene, alkynylene or arylene moiety bridging two or more atoms of the inorganic portion. In another related embodiment, the chromatography column is kept in a temperature range of about 5° C. to about 85° C. In another related embodiment, the mobile phase further includes a modifier added to the liquid $CO_2$ in a constant or gradient mode or both over an elution period or a fraction thereof. In another related embodiment, the modifier is a polar water-miscible organic solvent selected from the group consisting of methanol, ethanol or isopropanol, acetonitrile, acetone, tetrahydrofuran, mixtures thereof, and mixtures of water and any of these solvents. In another related embodiment, the gradient mode includes increasing or decreasing flow volume of the modifier. In another related embodiment, the elution period is less than 5 minutes. In another related embodiment, the gradient mode includes increasing the flow volume of the modifier from about 0% to about 50% (v/v $CO_2$) or any intervals therebetween. In another related embodiment, the gradient mode includes increasing the flow volume of the modifier from about 0% to about 25% (v/v of $CO_2$). In another related embodiment, the liquid $CO_2$ is in a supercritical state or a subcritical state or both. In another related embodiment, the detection includes determining the levels or the presence or absence of the one or more PAHs. In another related embodiment, the detection is by way of a mass spectrometer; Evaporative Light. Scattering (ELS) detector, Circular Dichroism (CD) detector, Flame Ionization Detector (FID) or a photodiode array detector (PDA). In another related embodiment, the sample includes an environmental sample, chemical sample, food sample, biological sample, or an extract thereof. In another related embodiment, the chromatography column is part of a chromatography system comprising a pre-column mobile phase dwell volume of about 75 to about 500 µL; wherein said pre-column mobile phase dwell volume is the volume of the mobile phase present in a fluidic connection between a junction at which the $CO_2$ and the modifier are mixed and the head of the chromatography column. In another related embodiment, the one or more PAHs are eluted from the chromatography column by the mobile phase with a flow rate of about 1 to 4 mL/min. In another related embodiment, the chromatography column has a length of about 50 to 150 mm and an internal diameter about 2 to 4 mm.

In another aspect, the subject technology relates to a chromatography method for detecting one or more polycyclic aromatic hydrocarbons (PAHs) in a sample including the steps of: (1) providing a sample containing one or more PAHs for analysis; wherein the sample is prepared with, extracted or dissolved in a diluent including at least 60% organic solvent, with the proviso that the sample is analyzed without a solvent exchange step, i.e., is not subject to a solvent exchange step; (2) applying the sample to a chromatography column with a solid stationary phase including inorganic or hybrid particles having a mean particle size of about 0.5 to about 3.5 microns, wherein said particles have a polar surface functionality, and wherein the particles retain said one or more PAHs; (3) eluting the one or more PAHs from the chromatography column by a mobile phase including a liquid $CO_2$ to form one or more eluted PAHs, wherein the mobile phase has a pre-column dwell volume of about 75 µL to about 500 µL, wherein said dwell volume includes a space within a fluidic or tubular connection between a junction at which two or more mobile phase solvents (e.g., liquid $CO_2$ and modifier) are mixed to the head of the column, and (4) detecting said one or more eluted PAHs by a mass spectrometer.

In another aspect, the subject technology relates to a method for detecting one or more PAHs including: (1) providing a sample comprising one or more PAHs for analysis; wherein the sample is prepared with, extracted or dissolved in a diluent comprising at least 60% organic solvent, with the proviso that the sample is not subject to a solvent exchange step; (2) applying the sample to a chromatography system including: (a) a column with a solid stationary phase comprising an inorganic or hybrid particle having a mean particle size of about 0.5 to about 3.5 microns, wherein said particle has a non-polar or polar/onpolar surface functionality, wherein said column has a length of about 50 to about 150 mm and an internal diameter about 2 to 4 mm, and wherein the solid stationary phase retains said one or more PAHs; (b) a pre-column mobile phase dwell volume of about 75 µL to about 500 µL; wherein pre-column dwell volume comprises a space within a fluidic or tubular connection between a junction at which two or more mobile phase solvents (e.g., the liquid $CO_2$ and the modifier) are mixed to the head of the column; and (c) a post-column mobile phase dwell volume of about 10 µL to about 450 µL; wherein said post-column dwell volume occupies a space within a fluidic or tubular connection between the end of the column and a detector; (3) eluting the one or more PAHs from the chromatography column by a mobile phase comprising a mixture of $CO_2$ and a modifier to form one or more eluted PAHs, wherein the mobile phase has a flow rate of about 1 to 4 mL/min; and (4) detecting said one or more eluted PAHs.

In another aspect, the subject technology relates to a kit for performing analysis or detecting one or more PAHs in a sample including: (a) a sample preparation device for preparing the sample including one or more PAHs for analysis; wherein the sample is prepared with, extracted or dissolved in a diluent comprising at least about 60% organic solvent, with the proviso that the sample is analyzed without a solvent exchange step; (b) a chromatography column with a solid stationary phase including inorganic, or hybrid particles having a mean particle size of 0.5 to 3.5 microns; wherein said particles have a non-polar or polar/non-polar surface functionality and retain said one or more PAHs; and (c) one or more standards for calibrating and facilitating the analysis and detection of the one or more PAHs.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology. Like reference numbers indicate like elements.

DETAILED DESCRIPTION

Figure 1:
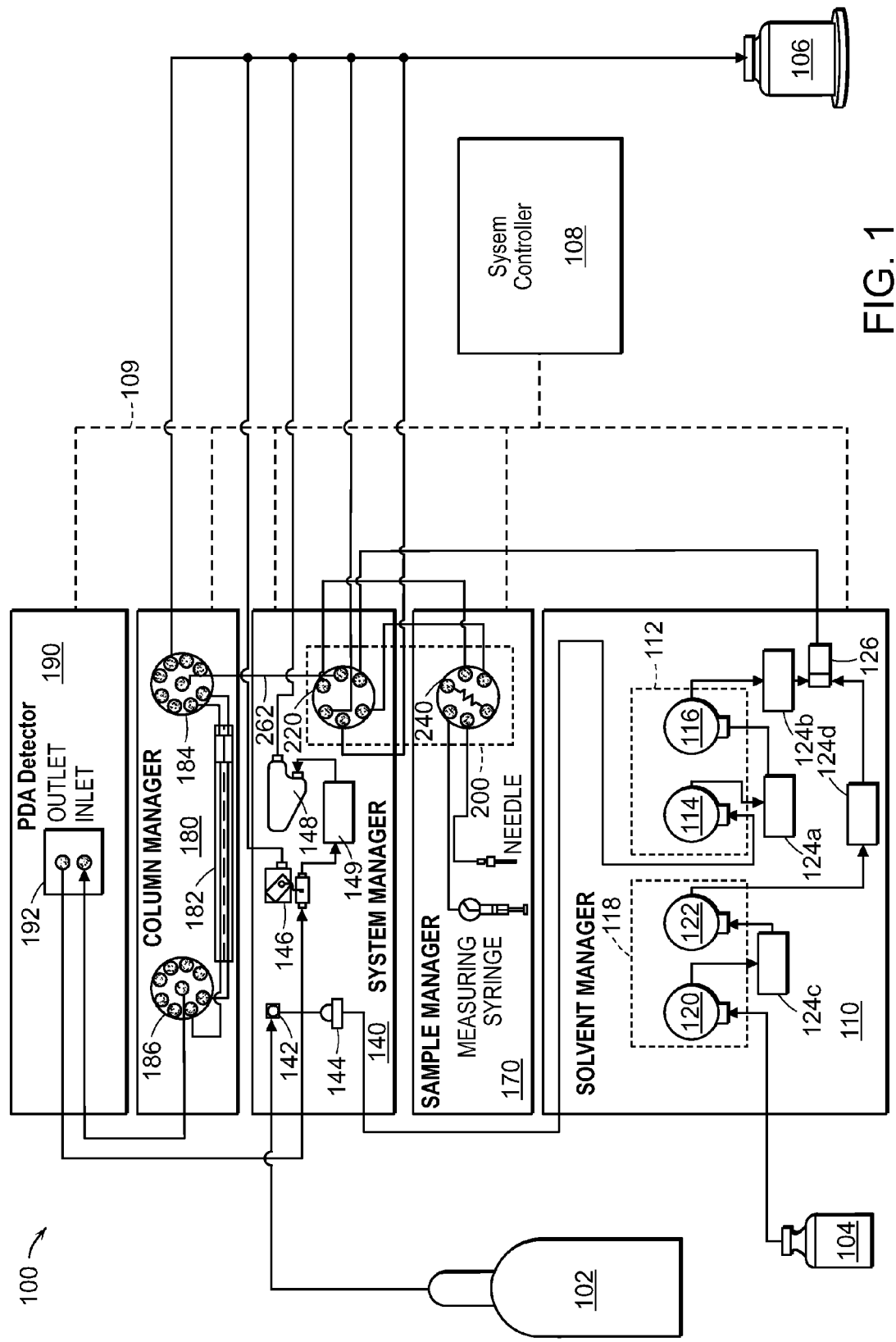
FIG. 1 is a schematic view of an exemplary $CO_2$-based system of the subject technology.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

To facilitate an understanding of the present subject technology, a number of terms and phrases are defined below:

Definitions:

A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Underlined, bold and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Unless otherwise indicated, all numbers expressing quantities such as flow volume or flow rate and so forth as used in the specification and claims are to be understood as being modified in all instances by the term "about." The term "about" as used herein in reference to quantitative measurements not including the measurement of the mass of a compound, refers to the indicated value plus or minus 10%.

As used herein, the term "analyte" refers to a compound or a mixture of compounds (i.e., a PAH or a mixture of PAHs) whose analytical levels or presence of absence in a sample is to be determined by the method or the system of the subject technology. PAHs are a large class of multi-ring structures that contain carbon and hydrogen atom. Exemplary PAHs include, but are not limited to, the compounds listed in Tables 1-2 and 4.

As used herein, the term "sample" or "extract" refers to a material which one desires to test for the analytical levels or the presence or absence of the analytes, i.e., PAHs. A sample may be obtained from a living source or a non-living source using conventional methods known in the art.

As used herein, the term "hybrid", as in "organic-inorganic hybrid material," includes inorganic-based structures wherein an organic functionality is integral to both the internal or "skeletal" inorganic structure as well as the hybrid material surface. The inorganic portion of the hybrid material can be, e.g., silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof. "Hybrid" includes inorganic-based structures wherein an organic functionality is integral to both the internal or "skeletal" inorganic structure as well as the hybrid material surface. The organic functionality includes organic functional groups which impart a certain chromatographic functionality to a stationary phase. Exemplary organic functional groups are substituted or unsubstituted aliphatic groups, alicyclic groups, heterocyclic groups, aromatic groups, amino groups and the like. Exemplary hybrid materials or particles are further described in U.S. Pat. Nos. 4,017,528; 6,528,167; 6,686,035 and 7,175,913; each of which is hereby incorporated herein by reference.

The term "aliphatic group" includes organic compounds characterized by straight or branched chains, typically having between 1 and 22 carbon atoms. Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, art amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, text-butyl, 3-thiopentyl, and the like. As used herein, the term "nitro" means —NO2; the term "halogen" designates —F, —Cl, —Br or —I; the term "thiol" means SH; and the term "hydroxyl" means —OH. The term "alkylamino" as used herein means an alkyl group, as defined above, having an amino group attached thereto. Suitable alkylamino groups include groups having 1 to about 12 carbon atoms, or from 1 to about 6 carbon atoms. The term "alkylthio" refers to an alkyl group, as defined above, having a sulfhydryl group attached thereto. Suitable alkylthio groups include groups having 1 to about 12 carbon atoms, or from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, or 1 to about 6 carbon atoms, e.g., methoxy, ethoxy, propoxy, tert-butoxy and the like. The terms "alkenyl" and "alkynyl" refer to unsaturated aliphatic groups analogous to alkyls, but which contain at least one double or triple bond respectively. Suitable alkenyl and alkynyl groups include groups having 2 to about 12 carbon atoms, or from 1 to about 6 carbon atoms.

The term "alicyclic, group" includes closed ring structures of three or more carbon atoms. Alicyclic groups include cycloparaffins or naphthenes which are saturated cyclic hydrocarbons, cycloolefins which are unsaturated with two or more double bonds, and cycloacetylenes which have a triple bond. They do not include aromatic groups. Examples of cycloparaffins include cyclopropane, cyclohexane, and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, —CF3, —CN, or the like.

The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —CF3, —CN, or the like. Suitable heteroaromatic and heteroalicyclic groups generally will have 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, indolyl, benzofuranyl, benzothiazolyl, tetrahydrofuranyl, tetrahydropyranyl, piperidinyl, morpholino and pyrrolidinyl.

The term "aromatic group" includes unsaturated cyclic hydrocarbons containing one or more rings. Aromatic groups include 5-and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, lower alkylcarboxyl, a nitro, a hydroxyl, —CF3, —CN, or the like.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone, e.g., C1-C30 for straight chain or C3-C30 for branched chain. In certain embodiments, a straight chain or branched chain alkyl has 20 or fewer carbon atoms in its backbone, e.g., C1-C20 for straight chain or C3-C20 for branched chain, or 18 or fewer. In some embodiments, the cycloalkyls have from 4-10 carbon atoms in their ring structure, and more or have 4-7 carbon atoms in the ring structure. The term "lower alkyl" refers to alkyl groups having from 1 to 6 carbons in the chain, and to cycloalkyls having from 3 to 6 carbons in the ring structure.

Moreover, the term "alkyl" (including "lower alkyl") as used throughout the specification and claims includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamide, nitro, trifluoromethyl, cyano, azide, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl (benzyl).

The term "aryl" includes 5-and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto. The term "aralkoxy" as used herein means an aralkyl group, as defined above, having an oxygen atom attached thereto. Suitable aralkoxy groups have 1 to 3 separate or fused rings and from 6 to about 18 carbon ring atoms, e.g., O-benzyl.

The term "amino," as used herein, refers to an unsubstituted or substituted moiety of the formula —NRaRb, in which Ra and Rb are each independently hydrogen, alkyl, aryl, or heterocyclyl, or Ra and Rb, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. An "amino-substituted amino group" refers to an amino group in which at least one of Ra and Rb, is further substituted with an amino group.

As used herein, the term "polar surface functionality," refers to one or more polar functional groups or moieties that are present on the surface of stationary phase particles, which impart polarity on the surface of the particles and permit them to interact with polar analytes or molecules. Exemplary polar functional groups include hydroxyl, aldehyde; amine; alcohol; ester; ketone; acids; acid anhydrides; metal salts; heteroatoms such as nitrogen, oxygen, the halogens, boron, phosphorus or sulphur; carbonyl, imine, oxime, N-oxide, diol, carboxy, nitrile, azide, diazonium, isonitrile, cyanate, isocyanate, or the sulphur analogues of the aforementioned O-containing groups. In this context, the polar functional group or moiety is bonded directly to surface of the particles through the inorganic structure of the inorganic particles or through the organic or inorganic portions of the hybrid particles. For example, the direct binding of the polar functional groups to the inorganic structure of the inorganic particles or to the inorganic portion of the hybrid particles may be through the modified silane or silanol monomers or through a carbon-silicon bond. In these particles, one or more of the functional groups (e.g., silanol) may be capped or not.

Exemplary particles with polar surface functionality are cyano-bonded particles in which the group bound to the surface containing a cyanoalkyl group (e.g. —$(CH_2)_n$-CN); diol-bonded particles in which the group bound to the surface containing a vicinal dihydroxyalkyl group (e.g., —$(CH_2)_n$-CHOH—$CH_2OH$); amino-bonded particles in which the group bound to the surface containing an amino-alkyl group (e.g., —$(CH_2)_n$-$NH_2$); or particles with free uncapped silanol groups and no additional polar groups being bound to the surface.

As used herein, the term "polar/non-polar surface functionality," as in particles having a polar/non-polar surface functionality, refers to particles that have a mixture of polar and non-polar functional groups on their surfaces. Exemplary non-polar functional groups are aliphatic groups. For example, the aliphatic group bound to the surface of the particles can be an alkyl chain between C1 and C18. The polar functional groups can be any of the ones described above, in an exemplary embodiment, a polar/non-polar surface functionality in particles refers to a mixture of non-polar functional groups and hydroxyl groups being present on the surfaces of the particles. For example, the hydroxyl groups may stem from the surface silanol groups that are uncapped.

Exemplary hybrid particles with polar/non-polar surface functionality are alkyl-bonded particles in which the group bound to the surface contains an alkyl chain (usually between C1 and C18); phenyl-bonded particles in which the group bound to the surface contains a phenyl group; or the like with the remaining functional (e.g., silanol) groups not being capped on the surface of the particles.

The "capped" stationary phase (or particle) (also known as"end-capped" stationary phase or material) is a bonded stationary phase (or particle) that has been treated with a second (usually less bulky) reagent, which is intended to react with remaining functional (e.g., silanol) groups which have not been substituted by the original reagent because of steric hindrance. Exemplary capping agents include, for example, tri organosiloxane.

As used herein, the term "calibrators" refer to preparations of PAH mixtures with quantitatively known contents that are used to prepare the necessary standards used to generate a calibration curve for PAH quantification.

As used herein, the term "controls" refers to preparations of PAH mixtures of known concentration, with PAH concentrations representing low, medium, and high levels of PAH concentrations within the calibration curve range. These are used to assess the analytical batch accuracy and acceptability.

As used herein, the term "tuning mixture" refers to a mixture of PAH in an appropriate solvent mixture used to optimize the performance of a mass spectrometer. A tuning mixture is often a mixture of known analytes with known concentrations that is used for tuning the mass spectrometer's performance.

As used herein, the term "internal standard" refers to a labeled PAH (e.g., isotopically or by fluorescence or the like) or closely related structural analogs of known concentration that can be added to the sample during preparation to increase the accuracy of PAH quantification.

As used herein, the term "derivatization reagents" refers to one or more compounds that can be reacted with PAHs to form a PAH-complex with increased mass spectroscopy sensitivity or improved chromatographic behavior relative to the underivatized PAH. Exemplary derivatization methods are alkylation, acylation and silylation, which are known in the art.

As provided above, the subject technology provides a novel method for the analysis of PAHs. In particular, the subject technology relates to the separation and analysis of PAHs using a $CO_2$-based chromatography system and method. As discussed in the background section, PAHs consist of multiple fused aromatic rings formed during incomplete combustion of various organic matters. Early observations in animal model displayed strong carcinogenic activity of these compounds which led to the conclusion that they are also carcinogenic to humans. It is for this reason that EU Scientific Committee for Food (SCF), the European Union (EU), and the US Environmental Protection Agency (EPA) recommend frequent monitoring of certain PAHs so that the human exposure to these compounds can be avoided or reduced.

Although, methods such as GC and LC can be used to analyze PAHs, the applicability of these methods is limited by issues such as long sample run time labor-intensive sample preparation requirements, generation of too much chemical waste which make these methods expensive and environmentally unfriendly. In addition, neither of GC or LC methods is applicable for analyzing a wide variety of PAHs. For example, it has been found that compounds with molecular weights greater than 300 Da are difficult to analyze on GC instruments because of their thermal degradation at high GC temperature. The LC methods have their own limitations. A proper separation and detection of PAHs on LC instruments require long run time, which in turn makes the method costly and results in generation of large volumes of toxic chemical waste.

The system and method of the subject technology can eliminate the shortcomings associated seen in the GC and LC methods. The use of the $CO_2$-based system of the subject technology provides a single viable technique that is cost-effective, sustainable and a green technology alternative that lowers the use of organic solvents provides faster analysis times and maintains chromatography data. However, as discussed earlier, the current SFC instruments and methods have many limitations including, for example, long sample run time, inaccurate or imprecise control over the mobile phase density and composition, inability to reliably deliver modifiers at low amounts (<5% of liquid $CO_2$), susceptibility to system pressure fluctuations and sample backflow, baseline noise, sample carryover, and lack of robustness, which prevent users from rapidly obtaining reproducible results.

The subject technology remedies the deficiencies associated with the existing chromatographic methods and provides a simple, sensitive and time- & cost-effective method and system for rapid separation and analysis of PAHs. The unique speed and resolution provided by the $CO_2$-based system and method of the subject technology allows for conducting an assay for PAHs that is rapid enough to use for routine screening. In addition, because the system does not require great amounts of expensive mobile phase solvents, the cost of running such assays is substantially low compared with other chromatography methods. As discussed above, the subject technology is based, in part, on the discovery that the $CO_2$-based system and method of the present disclosure provides a rapid separation of multiple PAHs in about four minutes. As shown in FIGS. 4-7, even at such a short run time, the peaks associated with the PAHs are surprisingly well-resolved with high signal to noise ratios. These results are attributable, in part, to the $CO_2$-based system of the subject technology, the column chemistry and/or the stationary phase particle sizes used therein. Several of these attributes are discussed below.

Accordingly, in some embodiments, the subject technology relates to a method of detecting one or more PAHs in a sample comprising the steps of: providing a sample including one or more PAHs; placing said sample in a $CO_2$-based system with one or more features described herein; subjecting the one or more PAHs to a separation column with one or more features described herein; eluting said one or more PAHs under a gradient of an organic solvent and liquid $CO_2$ to form one or more eluted PAHs, detecting said one or more PAHs with a suitable detection method.

The $CO_2$-Based System and the Method of Use

FIG. 1 illustrates an exemplary and simplified diagram of the $CO_2$-based system of the subject technology. As shown, the $CO_2$-based system 100 includes a plurality of stackable modules including a solvent manager 110; a system manager 140; a sample manager 170; a column manager 180; and a detector module 190.

By way of illustration and not limitation, in some embodiments, the solvent manager 110 is comprised of a first pump 112 which receives carbon dioxide ($CO_2$) from $CO_2$ source 102 (e.g., a tank containing compressed $CO_2$). The $CO_2$ passes through an inlet shutoff valve 142 and a filter 144 in the system manager 140 on its way to the first pump 112. The first pump 112 can comprise one or more actuators each comprising or connected to cooling means, such as a cooling coil and/or a thermoelectric cooler, for cooling the flow of $CO_2$ as it passes through the first pump 112 to help ensure that the $CO_2$ fluid flow is deliverable in liquid form. In some cases, the first pump 112 comprises a primary actuator 114 and an accumulator actuator 116. The primary and accumulator actuators 114, 116 each include an associated pump head, and are connected in series. The accumulator actuator 116 delivers $CO_2$ to the system 100. The primary actuator 114 delivers $CO_2$ to the system 100 while refilling the accumulator actuator 116.

According to certain embodiments, the solvent manager 110 also includes a second pump 118 for receiving an organic co-solvent (e.g., methanol, etc.) from a co-solvent source 104 and delivering it to the system 110. The second pump 118 can comprise a primary actuator 120 and an accumulator actuator 122, each including an associated pump head. The primary and accumulator actuators 120, 122 of the second pump 118 are connected in series. The accumulator actuator 122 delivers co-solvent to the system 100. The primary actuator 120 delivers co-solvent to the system 100 while refilling the accumulator actuator 122.

By way of illustration and not limitation, in some embodiments, transducers 124a-d are connected to outlets of the respective pump heads for monitoring pressure. The solvent manager 110 also includes electrical drives for driving the primary actuators 114, 120 and the accumulator actuators 116, 122. The $CO_2$ and co-solvent fluid flows are mixed at a tee 126 forming a mobile phase fluid flow that continues to an injection valve subsystem 200, which injects a sample slug for separation into the mobile phase fluid flow.

In some embodiments, the injection valve subsystem 200 is comprised of an auxiliary valve 220 that is disposed in the system manager 140 and an inject valve 240 that is disposed in the sample manager 170. The auxiliary valve 220 and the inject valve 240 are fluidically connected and the operations of these two valves are coordinated in such a manner as to reduce sample carry-over and system pressure perturbations occurring during injection. The reduced system pressure perturbations eliminate back flow in the column that may occur during injection and as the result of system pressure drops. The system manager 140 includes a valve actuator for actuating the auxiliary valve 220 and electrical drives for driving the valve actuations. Similarly, the sample manager 170 includes a valve actuator for actuating the inject valve and electrical drives for driving the valve actuations.

By way of illustration and not limitation, in some embodiments, from the injection valve subsystem 200, the mobile phase flow containing the injected sample slug continues through a separation column 182 in the column manager 180, where the sample slug is separated into its individual component parts. The column manager 180 comprises a plurality of such separation columns, and inlet and outlet switching valves 184, 186 for switching between the various separation columns.

After passing through the separation column 182, the mobile phase fluid flow continues on to a detector 192 (e.g., a flow cell/photodiode array type detector) housed within the detector module 190 then through a vent valve 146 and then on to a back pressure regulator 148 in the system manager 140 before being exhausted to waste 106. A transducer 149 is provided between the vent valve 146 and the back pressure regulator 148.

In embodiments, the back pressure regulator 148 is adjustable to control or modify the system fluid pressure. This can allow the pressure to be changed from run to run. The properties of $CO_2$ affect how quickly compounds are extracted from the separation column 182, so the ability to change the pressure can allow for different separation based on pressure. In certain embodiments, the back pressure regulator 148 can be used to maintain the system pressure in the range of about 1000 psi to about 9000 psi, or in the range of about 1000 psi to about 4000 psi, or at any particular pressure within these ranges.

By way of illustration and not limitation, in some embodiments, also shown schematically in FIG. 1 is a computerized system controller 108 that can assist in coordinating operation of the $CO_2$-based system 100. Each of the individual modules 110, 140, 170, 180, 190 also includes its own control electronics, which can interface with each other and with the system controller 108 via an Ethernet connection 109. The control electronics for each module can include non-volatile memory with computer-readable instructions (firmware) for controlling operation of the respective module's components (e.g., the pumps, valves, etc.) in response to signals received from the system controller 108 or from the other modules. In some embodiments, each module's control electronics can also include at least one processor for executing the computer readable instructions, receiving input, and sending output. The control electronics can also include one or more digital-to-analog (D/A) converters for converting digital output from one of the processors to an analog signal for actuating an associated one of the pumps or valves (e.g., via an associated pump or valve actuator). The control electronics can also include one or more analog-to-digital (A/D) converters for converting an analog signal, such as from system sensors (e.g., pressure transducers), to a digital signal for input to one of the processors. In some embodiments, some or all of the various features of these control electronics can be integrated in a microcontroller.

Figure 2:
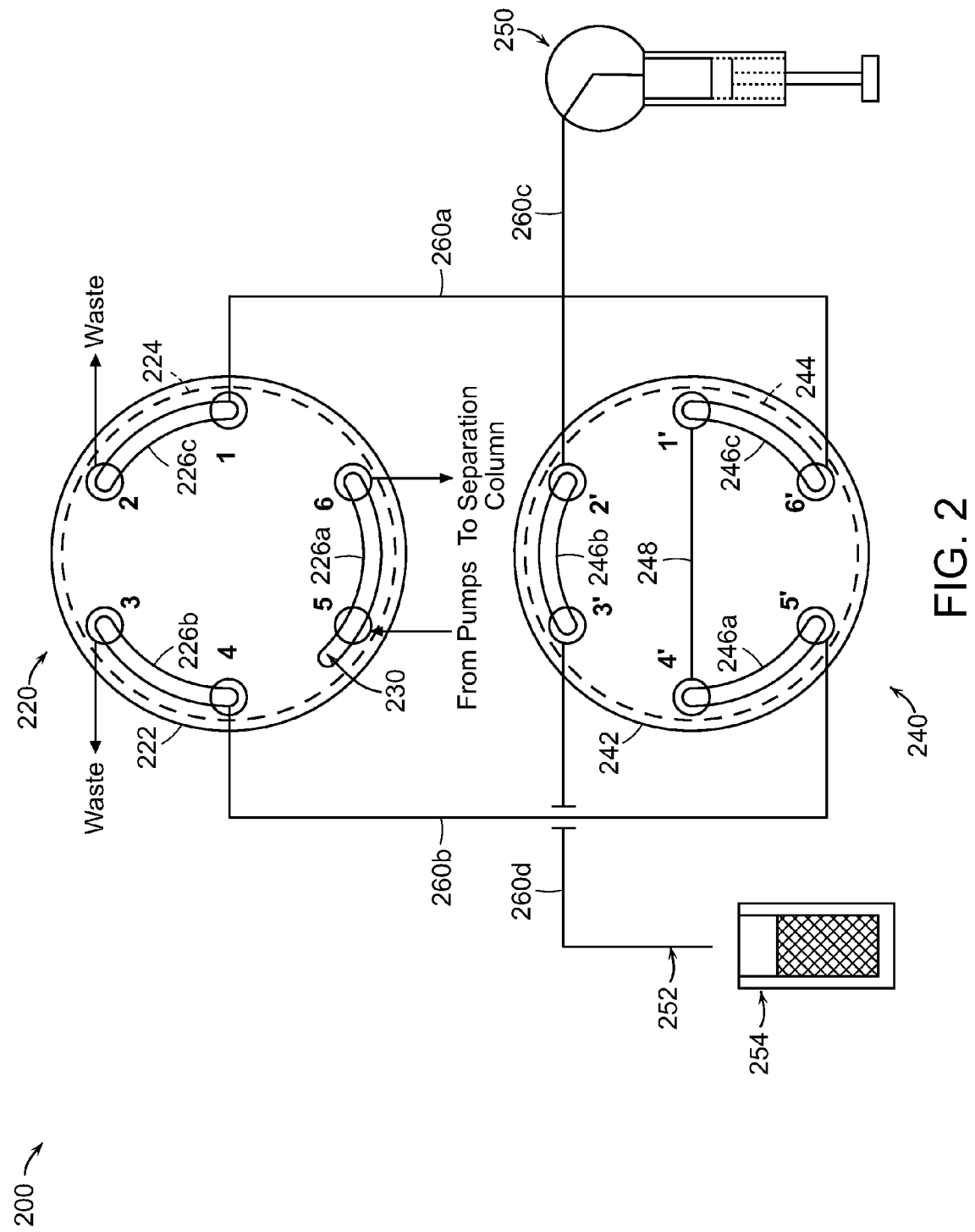
FIG. 2 is a schematic view of an exemplary injection valve for the $CO_2$-based system shown in FIG. 1.

In some embodiments, the injection valve subsystem 200 including the auxiliary valve 220 and the inject valve 240 is illustrated in FIG. 2. The auxiliary valve 220 is a rotary shear valve that includes an auxiliary valve stator 222 that has a plurality of ports, numbered 1 through 6 in FIG. 2, and an auxiliary valve rotor 224 that has a rotor interface, which includes three fluid conduits in the form of arcuate grooves 226a-c. When assembled, the rotor interface is urged into contact with the auxiliary valve stator 222, e.g., by pressure exerted on the auxiliary valve rotor 224 by a spring, to help ensure a fluid-tight seal therebetween. The ports 1-6 are configured to receive fittings (e.g., standard compression screw/ferrule type fittings) for coupling fluidic tubing to the auxiliary valve stator 222. In some embodiments, the auxiliary valve rotor 224 can be rotated to three discrete angular positions, relative to the auxiliary valve stator 222, to connect the rotor grooves 226a-c with different ones of the stator ports 1-6 to form different fluidic passageways. Notably, one of the grooves, groove 226a, includes an extended portion 230 which allows the auxiliary valve rotor 224 to be rotated to a position in which the groove 226a forms a fluidic pathway between stator ports 4 and 5, while ports 1-3 and 6 are dead ended.

By way of illustration and not limitation, in some embodiments, the inject valve 240 is another six-port rotary shear valve that includes an inject valve stator 242 having a plurality of ports, numbered 1' through 6' in FIG. 2, and an inject valve rotor 244. The inject valve rotor 244 has a rotor interface, which includes three fluid conduits in the form of arcuate grooves 246a-c. When assembled, the rotor interface is urged into contact with the inject valve stator 242, e.g., by pressure exerted on the inject valve rotor 244 by a spring, to help ensure a fluid-tight seal therebetween. In some embodiments, the ports 1'-6-' are configured to receive fittings (e.g., standard compression screw/ferrule type fittings) for coupling fluidic tubing to the inject valve stator 242. Port 1' is fluidically connected to port 4' via a sample loop 248 (e.g., fluidic tubing external to the inject valve stator 242). Port 2' is fluidically connected to a metering syringe 250 and port 3' is connected to a needle 252. The metering syringe 250 and needle 252 are disposed within the sample manager 170 and are operable to aspirate sample from vials 254 also in the sample manager 170. Port 5' of the inject valve 240 is connected to port 4 of the auxiliary valve 220, and port 6' of the inject valve 240 is connected to port 1 of the auxiliary valve 220. The connections between port 2' and the syringe 250, between port 3' and the needle 252, between port 5' and port 4, and between port 6' and port 1 are made via the fluidic tubing 260a-d.

In some embodiments, the inject valve rotor 244 can be rotated to two discrete angular positions, relative to the inject valve stator 242, to connect the rotor grooves 246a-c with different ones of the stator ports 1'-6' to form different fluid passageways.

The coordinated operation of the auxiliary and inject valves 220, 240 helps to improve performance of the $CO_2$-based system 100 by reducing the amount of sample carryover and can also help to reduce system pressure perturbations occurring during injection. As a result, the separation column 182 may be subjected to lower pressure pulses, potentially increasing the life of the column 182.

In short, during an injection, sample inside the sample loop 248 is brought online to the fluidic tubing 260a, 260b connecting the auxiliary and inject valves 220, 240 while mobile phase fluid comprising high pressure $CO_2$ flows directly from the pumps 112, 118 to the separation column 182 via the auxiliary valve 220. The auxiliary valve 220 then allows the fluidic tubing 260a, 260b, comprising gaseous $CO_2$ and sample, to fill and compress with the mobile phase fluid before introducing the fluid into the high pressure (e.g., about 1500 psi to about 9000 psi) stream. The combination of these two actions can help to reduce (e.g., eliminate) carry-over anomalies and system pressure pulses when introducing sample into the high pressure stream. The combination of these two actions can help to reduce (e.g., eliminate) carry-over anomalies and system pressure pulses when introducing sample into the high pressure stream. An exemplary process for operating the $CO_2$ based system of the subject technology is as follows.

Step 1: Sample Manager Setup

First, the sample manager 170 (FIG. 1) sets up internally by running various checks and setup procedures.

Step 2: De-Compress Sample Loop

At the start of an injection, the inject valve rotor 244 (FIG. 2) is in its inject position (from a previous injection), and the sample manager 170 triggers the auxiliary valve 220 to turn its rotor 224 (60 degrees counterclockwise) to its load position. This allows the sample loop 248 on the inject valve 240 and the fluidic tubing 260a, 260b connecting the auxiliary and inject valves 220, 240 to vent to atmosphere. At this time, the mobile phase fluid is permitted to flow directly from the pumps 112, 118 to the separation column 182 via the auxiliary valve 220. This pressurizes a flow path 262 (FIG. 1) between the auxiliary valve 220 and the separation column 182 to a system pressure of about 1500 psi to about 9000 psi.

Step 3: Aspirate Partial Loop with Needle Overfill (PLNO) Sample

Next, the sample manager 170 moves the needle 252 to a programmed vial position, aspirates an air gap, aspirates pre-sample buffer from the vial 254, aspirates the programmed amount of sample from the vial 254, aspirates post-sample buffer from the vial 254 (see FIG. 2), and then removes the needle 252 from the vial and returns it toward the inject port. A final air gap is aspirated in this position. Then, the sample manager metering syringe 250 meters the sample slug so that the injection volume is past port 2'. The syringe 250 then dispenses 0.5 µL to take out any compliance or backlash within the system.

Step 4: Load Sample into the Sample Loop

The inject valve rotor 244 is then moved (60 degrees clockwise) to place the inject valve 240 in its load position, with the sample loop 248 in fluidic communication with the meter and needle ports 2', 3' (FIG. 2), and the programmed sample volume is moved into the sample loop 248.

Step 5: Inject Sample into Fluidic Tubing

Within the sample manager 170, the inject valve rotor 244 is rotated (60 degrees counterclockwise) to the inject position, introducing sample into residual gaseous $CO_2$ and programmed co-solvent from the previous injection in the fluidic tubing 260a, 260b connecting the auxiliary and injection valves 220, 240.

Step 6: Bring $CO_2$ Online/Inject Sample into System

The sample manager 170 then triggers the auxiliary valve rotor 224 to turn (45 degrees clockwise) to place the auxiliary valve rotor 224 in its fill position to make the connection between ports 4 and 5 only. At this time, all other connections are dead ended. This action redirects the flow of mobile phase fluid comprising $CO_2$ and any programmed co-solvent from the pumps 112, 118 through the sample loop 248 and dead ends against port 1 of the auxiliary valve 220. The auxiliary valve rotor 224 remains in the fill position for a calculated pause time (based on mobile phase flow rate, sample loop 248 volume, and injection volume) until the fluidic tubing 260a, 260b and sample loop 248 are filled with liquid mobile phase comprising $CO_2$ and any programmed co-solvent. During this time, the pressure in the flow path 262 between the auxiliary valve 220 and the separation column 182 remains substantially at system pressure (e.g., within 500 psi) due to the resistance to flow through the separation column 182 (FIG. 1). In this regard, the flow path 262 typically experiences a pressure drop of less than 500 psi while connections are dead ended.

Step 7: Inject Sample into System

The auxiliary valve rotor 224 is then rotated (an additional 15 degrees clockwise) to the inject position, completing all port connections. This action redirects the flow of mobile phase comprising high pressure $CO_2$ and any programmed co-solvent through the sample manager 170 and injects compressed sample into the high pressure system 100.

Step 8: Wash the Needle

With the auxiliary and inject valve rotors 224, 244 in their respective inject positions, the sample manager 170 washes the outside and inside of the needle 252 after sample is injected. The wash syringes dispense a programmed amount of strong and weak washes through the inject valve 240 and out through the needle 252.

Figure 3:
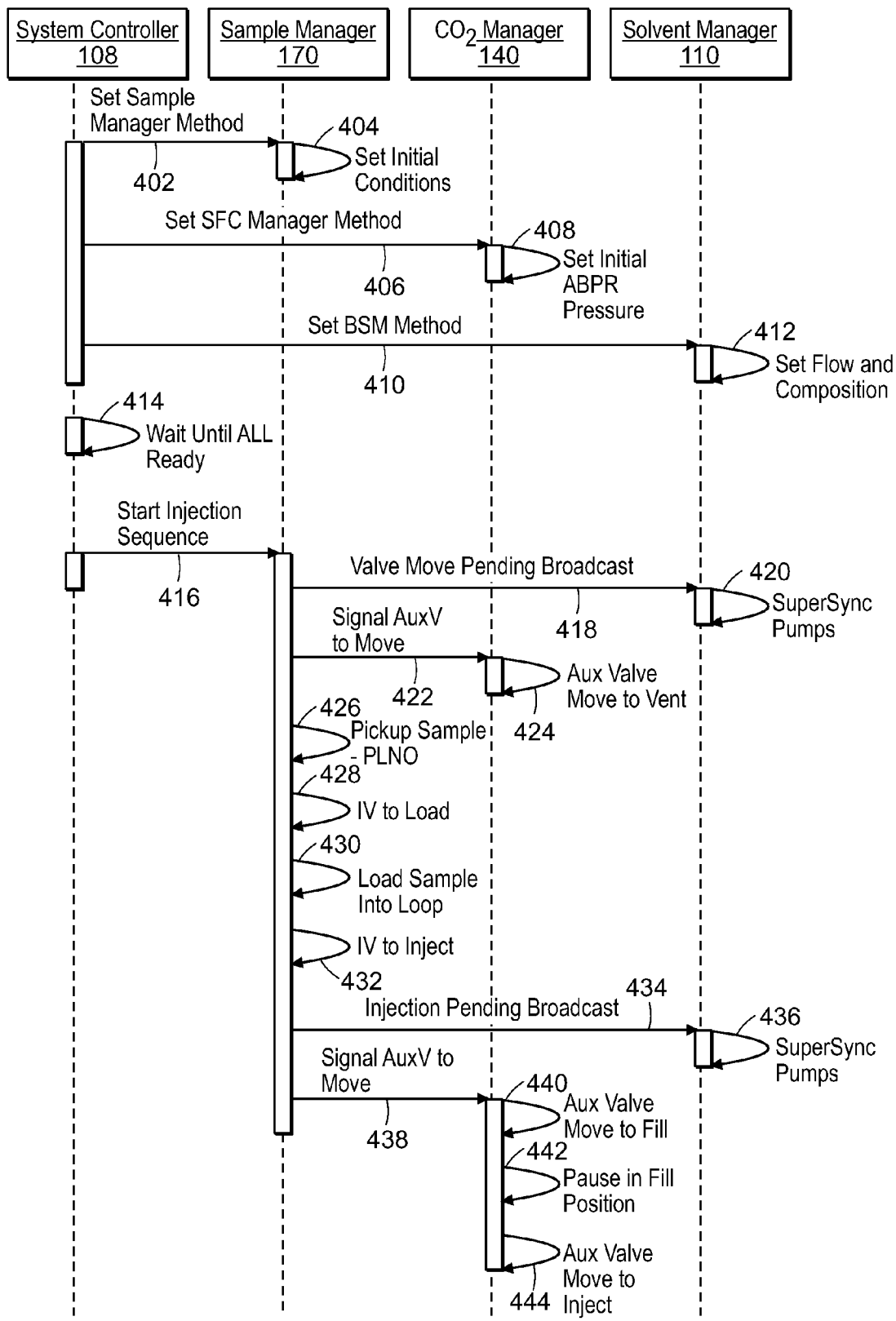
FIG. 3 is an exemplary diagram showing a software timing mode for developing an injection sequence in the $CO_2$-based system of the subject technology.

By way of illustration and not limitation, FIG. 3 depicts a software timing diagram used to develop the injection sequence, according to some embodiments of the subject technology. With reference to FIG. 3, the system controller 108 signals (402) the sample manager 170, via the Ethernet connection, triggering the sample manager 170 to rotate (404) the inject valve rotor 244 to its insect position. The system controller 108 also signals (406) the system manager 140 to set (408) the back pressure regulator 148 to provide the desired pressure setting. Finally, the solvent manager 110 is triggered (410) by the controller 108 to set (412) the flow and composition of the mobile phase solvent. The system controller 108 waits (414) until the sample manager 170, system manager 140, and solvent manager 110 have performed their respective tasks and are ready to perform a sample injection.

Then, the system controller 108 signals (416) the sample manager 170 to start the injection sequence. In response, the sample manager 170 signals (418) the solvent manager 110 to synchronize (420) the pumps (positioning plungers within the actuators in a predetermined start point position). The sample manager 170 then signals (422) the system manager 140 to move (424) the auxiliary valve rotor 224 to its load position. Next, the sample manager 170 executes the step of aspirating the PLNO sample (426), and, then, drives (428) the inject valve rotor 244 to its load position. After sample is loaded (430) into the sample loop 248, the sample manager 170 drives (432) the inject valve to the inject position. The sample manager 170 then signals (434) the solvent manager 110 to again synchronize (436) the actuator plungers.

Finally, the sample manager 170 signals (438) the system manager 140 to execute the final movements of the auxiliary valve rotor 224. In response, the system manager 140 drives (440) the auxiliary valve rotor 224 to its fill position, and then pauses (442) it in the fill position (to fill and pressurize the fluidic tubing 260a, 260b with liquid mobile phase comprising $CO_2$ and programmed co-solvent). Then, the system manager 140 drives (444) the auxiliary valve rotor 224 to its inject position (for injection of the sample into high pressure system).

In some embodiments, the system pressure of the $CO_2$-based system of the subject technology, which is the pressure of the liquid as it exits the pump, is from about 4000 psi to about 9000 psi. In an embodiment, the system pressure is any pressure between the range of about 1000 psi to about 9000 psi. In some embodiments, the system pressure controller of the $CO_2$-based system of the subject technology provides and maintains steady pressure levels, and provides accurate and reproducible pressure gradients.

In some embodiments, the pressure at the exit of the system, as controlled by the automated backpressure regulator (ABPR) in the $CO_2$-based system of the subject technology is from about 1000 psi to 9000 psi. In an embodiment, the backpressure is any pressure between the range of about 1000 psi to about 9000 psi. In another embodiment, the ABPR is set at 1700 psi, 2200 psi, 2500 psi, 2900 psi, 3200 psi, 3500 psi. In some embodiments, the ABPR of the $CO_2$-based system of the subject technology provides steady pressure levels and improved pressure gradients.

In some embodiments, the pre-column mobile phase dwell volume of the $CO_2$-based system of the subject technology is about 75 µL to about 500 µL. The pre-column mobile phase dwell volume is the volume of mobile phase present in a fluidic connection or piping between a junction at which the $CO_2$ and the modifier are mixed and the head of the chromatography column. In an embodiment, the pre-column mobile phase dwell volume is about 100 µL, or about 150 µL, or about 200 µL, or about 250 µL, or about 300 µL, or about 320 µL, or about 350 µL, or about 400 µL or about 450 µL, or any volumes therebetween.

In some embodiments, the internal diameter of the fluidic connection that holds the pre-column mobile phase dwell volume is about 50 µm to about 400 µm. In some embodiments, the internal diameter of the fluidic connection that holds the pre-column mobile phase dwell volume is about 75 µm, or about 100 µm, or about 130 µm, or about 150 µm, or about 200 µm, or about 250 µm, or about 300 µm, or about 350 µm, or about 375 µm, or any lengths therebetween.

In some embodiments, the post-column mobile phase dwell volume of the $CO_2$-based system of the subject technology is about 10 µL to about 450 µL. The post-column mobile phase dwell volume is the volume of mobile phase present in a fluidic connection or piping between the end of the column and the detector. In an embodiment, the post-column mobile phase dwell volume is about 10 µL, about 20 µL, about 30 µL, about 50 µL, about 90 µL, or about 120 µL, or about 150 µL, or about 200 µL, or about 250 µL, or about 300 µL, or about 350 µL, or about 400 µL or any volumes therebetween.

In some embodiments, the internal diameter of the fluidic connection that holds the post-column mobile phase dwell volume is about is about 50 µm to about 400 µm. In some embodiments, the internal diameter of the fluidic connection that holds the post-column mobile phase dwell volume is about 75 µm, or about 100 µm, or about 130 µm, or about 150 µm, or about 200 µm, or about 250 µm, or about 300 µm, or about 350 µm, or about 375 µm, or any lengths therebetween.

In some embodiments, the volume of the volume of sample needed to be injected to the $CO_2$-based system of the subject technology is from about 0.1 µL, to 20 µL, or any particular volume in between this range. For example, in an embodiment, the sample volume injected is 1 µL. However, those of skill in the art appreciate that the volume of sample to be injected depends primarily on the concentration of the analytes in that sample and also on what type of detection method being used. For example, if MS (Mass Spectroscopy) is the detection method used in tandem with the $CO_2$-based system of the subject technology, smaller injection volumes are typically required. In some embodiments, the $CO_2$-based system of the subject technology when in tandem with an MS/MS can facilitate detection of analytes in picogram (pg, one trillionth ($10^{-12}$) of a gram) ranges.

In the subject technology, the temperature fluctuations in the pumping systems which may result in system pressure fluctuations are reduced or eliminated, which leads to a reduced baseline noise of chromatograms of the $CO_2$-based system of the subject technology.

Alternatively or in addition, the $CO_2$-based system of the subject technology minimizes the consumption of mobile phase solvents (e.g. methanol, acetonitrile, etc.) thereby generating less waste for disposal and reducing the cost of analysis (by more than 100 fold, in some cases) per sample.

The Column Chemistry

In various embodiments, the solid stationary phase of the chromatography columns of the $CO_2$-based system of the subject technology includes porous inorganic or inorganic/organic hybrid particles with the mechanical stability and structural integrity required to withstand the operating pressures of the system.

Inorganic particles suitable for use in the system and method of the subject technology include silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof. In some embodiments, such inorganic particles may have no surface modifications. For example, without surface modifications, silica is characterized by the presence of silanol groups on its surface. In some other embodiments, the inorganic particles, e.g., silica, may have been surface modified. For example, silica can be surface modified or derivatized with an organic polar or non-polar functional group such as butyl ($C_4$), octyl ($C_8$), octadecyl ($C_{18}$), $C_{30}$, phenyl, amino, cyano, etc. A suitable commercially available column that includes such particle is, for example, the "ACQUITY UPC$^2$ HSS C18 SB column, Waters Corporation, Milford, Mass."

Hybrid particles suitable for use in the system and method of the subject technology include an inorganic portion such as, e.g., alumina, silica, titanium or zirconium oxides, or ceramic material; and an organic portion bonded to one or more atoms of the inorganic portion. Exemplary hybrid materials are disclosed in U.S. Pat. No. 4,017,528, the text of which is incorporated herein by reference.

In some embodiments, the organic portion of the hybrid particles is a C1-C18 aliphatic or aromatic moieties (which may additionally be substituted with alkyl, aryl, cyano, amino, hydroxyl, diol, nitro, ester, ion exchange or embedded polar functionalities) or a substituted or unsubstituted C1-C18 alkylene, alkenylene, alkynylene or arylene moiety. In one embodiment where the inorganic portion is silica, "hybrid silica" refers to a material having the formula $SiO_2(R^2_pR^4_qSiO_t)_n$ or $SiO_2/[R^6R^2_rSiO_t)_m]_n$ (disclosed in U.S. Pat. Nos. 7,919,177; 7,223,473, and 6,686,035, each of which is hereby incorporated herein by reference) wherein $R^2$ and $R^4$ are independently $C_1$-$C_{18}$ aliphatic or aromatic moieties (which may additionally be substituted with alkyl, aryl, cyano, amino, hydroxyl, diol, nitro, ester, ion exchange or embedded polar functionalities), R6 is a substituted or unsubstituted C1-C18 alkylene, alkenylene, alkynylene or arylene moiety bonded to one or more silicon atoms or bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, or alternatively, 0.1 to 1, or alternatively 0.2 to 0.5. $R^2$ may be additionally substituted with a functionalizing group R.

The functionalizing group R includes organic functional groups which impart a certain chromatographic functionality to a chromatographic stationary phase, including, e.g., octadecyl (C18) or phenyl. Such functionalizing groups are present in, e.g., surface modifiers such as disclosed herein which are attached to the base material, e.g., via derivatization or coating and later crosslinking, imparting the chemical character of the surface modifier to the base material. In an embodiment, such surface modifiers have the formula Za(R')bSi—R, where Z=Cl, Br, I, C1-C5 alkoxy, dialkylamino, e.g., dimethylamino, or trifluoromethanesulfonate; a and b are each an integer from 0 to 3 provided that a+b=3; R' is a C1-C6 straight, cyclic or branched alkyl group, and R is a functionalizing group. R' may be, e.g., methyl, ethyl, propyl, isopropyl, butyl, t-butyl, sec-butyl, pentyl, isopentyl, hexyl or cyclohexyl; in an embodiment, R' is methyl.

The porous inorganic/organic hybrid particles possess both organic groups and silanol groups which may additionally be substituted or derivatized with a surface modifier. "Surface modifiers" include (typically) organic functional groups which impart a certain chromatographic functionality to a chromatographic stationary phase. Surface modifiers such as disclosed herein are attached to the base material, e.g., via derivatization or coating and later crosslinking, imparting the chemical character of the surface modifier to the base material. In one embodiment, the organic groups of the hybrid particle react to form an organic covalent bond with a surface modifier. The surface modifiers can form an organic covalent bond to the particle's organic group via a number of mechanisms well known in organic and polymer chemistry including but not limited to nucleophilic, electrophilic, cycloaddition, free-radical, carbene, nitrene, and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur, and the halogens. In addition, carbon-silicon and carbon-oxygen-silicon bonds are defined as organic covalent bonds, whereas silicon-oxygen-silicon bonds that are not defined as organic covalent bonds.

In some embodiments, the solid stationary phase of the separation columns of the subject technology includes a monolith, particles, porous particles, and/or superficially porous particles. Particles can be spherical or non-spherical. The solid stationary phase can include silica, inorganic silica, and/or metal oxide. In some embodiments, the column is equipped with one or more frits to contain the stationary phase material. In embodiments in which the stationary phase material is monolithic, the housing may be used without the inclusion of one or more frits.

The solid stationary phase includes, for example, particles having a mean size within the range of about 0.5-3.5 microns, though a smaller or larger size could be selected if appropriate for a desired application. In various embodiments, the mean particle size is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4 or 3.5 microns. In general, particle size can be selected in view of the desired pressure and/or flow rate. For example, larger particle size can be used to achieve consistent pressure from a column head to an end during high pressurized digestion. Alternatively, smaller particle sizes result in higher flow rates, higher efficiency, which yield faster, more sensitive separations. The solid stationary phase can include pores having a mean pore volume within the range of 0.1-2.5 cm/g. In various examples, the mean pore volume is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, or 2.5 cm/g. In some embodiments, porous particles may be advantageous because they provide a relatively large surface area (per unit mass or column volume) for protein coverage at the same time as the ability to withstand high pressure.

The solid stationary phase can include pores having a mean pore diameter within the range of 100-1000 Angstroms. For example, in some embodiments, the mean pore diameter of the solid stationary phase particles is about 100, 200, 300, 400, 500, 600, 700, 800, 900, 1000 Angstroms, or any value or range therebetween.

In certain embodiments, the chromatography or separation column of the subject technology includes (a) a column having a cylindrical interior for accepting a packing material, and (b) a packed chromatographic bed comprising a porous material comprising an organosiloxane/SiO2 material having the formula $SiO_2(R^2_pR^4_qSiO_t)_n$ or $SiO_2/[R^6(R^2_rSiO_t)_m]_n$, as described above, wherein $R^2$ and $R^4$ are independently C1-C18 aliphatic, styryl, vinyl, propanol, or aromatic moieties, $R^6$ is a substituted or unsubstituted $C_1$-$C_{18}$ alkylene, alkenylene, alkynylene or arylene moiety bridging two or more silicon atoms, p and q are 0, 1 or 2, provided that p+q=1 or 2, and that when p+q=1, t=1.5, and when p+q=2, t=1; r is 0 or 1, provided that when r=0, t=1.5, and when r=1, t=1; m is an integer greater than or equal to 2, and n is a number from 0.03 to 1, said porous hybrid silica chromatographic matrix having a chromatographically-enhancing pore geometry and average pore diameters of about 100 to 300 Å. In an embodiment, the porous particles of hybrid silica have been surface modified. In another embodiment, the particles have been surface modified by a surface modifier selected from the group consisting of an organic group surface modifier, a silanol group surface modifier, a polymeric coating surface modifier, and combinations thereof. In another embodiment, the surface modifier has the formula Za(R')bSi—R, where Z=Cl, Br, I, $C_1$-$C_5$ alkoxy, dialkylamino or trifluoromethanesulfonate; a and b are each an integer from 0 to 3 provided that a+b=3; R' is a $C_1$-$C_6$ straight, cyclic or branched alkyl group, and R is a functionalizing group.

The functionalizing group R may include alkyl, alkenyl, alkynyl, aryl, cyano, amino, diol, nitro, cation or anion exchange groups, or alkyl or aryl groups with embedded polar functionalities. Examples of suitable R functionalizing groups include C1-C30 aryl, including $C_1$-$C_{20}$, such as octyl ($C_8$), octadecyl ($C_{18}$), and triacontyl ($C_{30}$); alkaryl, e.g., $C_1$-$C_4$-phenyl, cyanoalkyl groups, e.g., cyanopropyl; diol groups, e.g., propyldiol; amino groups, e.g., aminopropyl; and alkyl or aryl groups with embedded polar functionalities, e.g., carbamate functionalities such as disclosed in U.S. Pat. No. 5,374,755, the text of which is incorporated herein by reference. In an embodiment, the surface modifier is an organotrihalosilane, such as octyltrichlorosilane or octadecyltrichlorosilane. In another embodiment, the surface modifier may be a halopolyorganosilane, such as octyldimethylchlorosilane or octadecyldimethylchlorosilane.

In another embodiment, the hybrid particle's organic groups and silanol groups are both surface modified or derivatized. In another embodiment, the particles are surface modified by coating with a polymer. In certain embodiments, surface modification by coating with a polymer is used in conjunction with silanol group modification, organic group modification, or both silanol and organic group modification.

Polymer coatings are known in the literature and may be provided generally by polymerization or polycondensation of physisorbed monomers onto the surface without chemical bonding of the polymer layer to the support (type I), polymerization or polycondensation of physisorbed monomers onto the surface with chemical bonding of the polymer layer to the support (type II), immobilization of physisorbed prepolymers to the support (type III), and chemisorption of presynthesized polymers onto the surface of the support (type IV). See, e.g., Hanson et al., J. Chromat. A656 (1993) 369-380, the text of which is incorporated herein by reference. As noted above, coating the hybrid material with a polymer may be used in conjunction with various surface modifications described in U.S. Pat. Nos. 7,919,177; 7,223,473, and 6,686,035, each of which is hereby incorporated herein by reference. Additional inorganic/organic hybrid particles are disclosed in WO2010141426, which is hereby incorporated herein by reference.

Exemplary suitable commercially available columns that include such inorganic/organic hybrid particles include, for example, the "ACQUITY UPC$^2$ ethylene bridged hybrid (BEH), BED 2-EP, and charged surface hybrid (CSH) C18 SB columns, Waters Corporation, Milford, Mass."

In one exemplary embodiment, the particles used in the separation columns of $CO_2$-based system of the subject technology have the following specifications:

| Chemistry | Particle Shape | Particle Size (μm) | Pore Size (Å) | Surface Area (m²/g) | Carbon Load (%) | Endcapped |
|---|---|---|---|---|---|---|
| Hybrid particles with a polar surface functionality (e.g., BEH 2-ethylpridine) | Spherical | 1.7, 3.5 | 135 | 185 | 9 | No |
| Hybrid particles with surface silanol groups but no additional surface functionality (e.g., BEH) | Spherical | 1.7, 3.5 | 135 | 185 | N/A | N/A |
| Hybrid particles with surface modification/ polymer coating (e.g., CSH Flouro-phenyl) | Spherical | 1.7, 3.5 | 135 | 185 | 10 | No |
| Inorganic silica particles with a surface functionality (e.g., HSS $C_{18}$ SB) | Spherical | 1.7, 3.5 | 100 | 230 | 8 | No |

In some embodiments, the depending on the complexity and nature of the sample components, the separation is accomplished using a hybrid material stationary phase modified with an alternate ligand (polar, non-polar, or ionic), or one with no additional surface modification at all. Additionally, the separation could be achieved on various particles sizes below 5 μm in diameter. In some embodiments, the internal diameter (ID) of the chromatography column of the subject technology is between about 1 mm to 5 mm, or between about 2 mm to 4 mm. In an embodiment, the ID of the column is about 3 mm. In some embodiments, the length of the chromatography column of the subject technology is between about 30 mm to 200 mm or between about 50 mm to 150 mm. In an embodiment, the length of the chromatography column is 50 mm. In another embodiment, the length of the chromatography column is 150 mm.

In some embodiments, depending on the column dimension chosen and optimization necessary, the flow rate of the mobile phase is set between about 0.1 mL/min to 4 mL/min, or any intervals there between, e.g., between about 0.5 mL/min to 3.5 mL/min, with a backpressure regulator setting of about 1000-9000 psi or about 1000-4000 psi. In other embodiments, the temperature at which the chromatography column operates is adjusted to optimize the analyte separations with a practical working range of about 5° C. to 85° C., or any specific temperature within this range. In some embodiments, the column compartment temperature ranges from about 40° C. to 70° C. In one embodiment, the column compartment temperature ranges from about 20° C. to 70° C. In another embodiment, the column compartment temperature is kept at about 20° C. or at about 85° C. or at any specific temperature between about 5° C. to 85° C.

The Mobile Phase Solvent

In some embodiments, the method of the subject technology relates to method of detecting the presence or absence or levels of an analyte or a solute (i.e., a PAH or a mixture of PAHs) in a mixture. Thus, according to certain embodiments of the subject technology, a solution having an analyte is contacted with a porous material of the separation column under conditions that allow for sorption of the analyte to the porous material. The analyte can be, e.g., any molecule having a hydrophobic, hydrophilic, or ionic interaction or a combination of two or three of these interactions. The porous material having the sorbed analyte is eluted with a solvent under conditions so as to desorb the analyte from the porous material. The level of the desorbed solute (e.g., eluted PAHs) present in the solvent eluted from the separation column after the elution can then be detected using a suitable detection method.

In general, liquid $CO_2$ is used as the main mobile phase solvent of the subject technology to desorb the solute(s). In some embodiments, the liquid $CO_2$ is in a supercritical state. In some embodiments, the liquid $CO_2$ is in a subcritical state. In some embodiments, the physical state of the liquid $CO_2$ changes between supercritical and subcritical or vice versa. Due to its miscibility, the $CO_2$ solvent can be combined with one or more modifiers (co-solvents) for more effective desorption or elution of the analytes from the chromatography column.

In some embodiments, suitable modifiers to be combined with the $CO_2$ mobile phase include, e.g., polar water-miscible organic solvents, such as alcohols, e.g., methanol, ethanol or isopropanol, acetonitrile, acetone, and tetrahydrofuran, or mixtures of water and any of these solvents. In other embodiments, the modifiers include, e.g., nonpolar or moderately polar water-immiscible solvents such as pentane, hexane, heptane, xylene, toluene, dichloromethane, diethylether, chloroform, acetone, dioxane, THF, MTBE, ethylacetate or DMSO. Mixtures of these modifiers are also suitable. In some embodiments, modifiers or modifier mixtures must be determined for each individual case. A suitable modifier can be determined by one of ordinary skill in the art without undue experimentation, as is routinely done in chromatographic methods development.

In one embodiment, the ratio of a modifier to $CO_2$ (v/v) is between about 0.0001 to 1 to about 1 to 1. In another embodiment, this ratio of modifier to $CO_2$ (v/v) is between about 0.001 to 1 to about 1 to 1, or any ratios in between. In certain embodiments, the amount of the modifier added to $CO_2$ is constant or changes in a gradient mode (increasing or decreasing), or is a combination of both, during the elution period. In certain other embodiments, the modifier is added to the $CO_2$ mobile phase at a constant rate of, for example, 8%, or 10%, or 20%, or 25% over the elution period.

In some embodiments the modifier is added, in an increasing gradient mode, from about 0% to 50% (v/v to $CO_2$), or from about 8% to 33%, or from about 6% to 35%, or from about 4% to 37%, or from about 9% to 40% (v/v to $CO_2$), or from about 8% to 27%, or from about 11%-30%, or any other intervals within the 0% to 50% (v/v to $CO_2$) range, over the elution period.

In some embodiments the modifier is added, in a decreasing gradient mode, from about 50% to 0% (v/v to $CO_2$), or from about 33% to 8%, or from about 35% to 6%, or from about 37% to 4%, or from about 40% to 9% (v/v to $CO_2$), or from about 27% to 8%, or from about 30%-11%, or any other intervals within the 50% to 0% (v/v to $CO_2$) range, over the elution period. In some embodiments, the modifier is added to the $CO_2$ mobile phase in a gradient of 0% to about 50% (v/v $CO_2$) (or any ascending percentage range within 0% to 50%) in about 2 to 4 min (or any fraction of time within this range) with a hold period at a constant modifier percentage at the beginning, at the end or at any time during the elution period. For example, in an embodiment, the hold period is for about 0.1 to 3 min (or any fraction of time within this range) at constant modifier volume of e.g., 5%, 10%, 15%, 20%, 30%, 40% (v/v to $CO_2$) or more. In some embodiments, the modifier is added in gradients of 0% to about 70% or less (v/v $CO_2$), 0% to about 50% or less (v/v to $CO_2$), or 0% to about 30% or less (v/v to $CO_2$) over the elution period.

In some embodiments, the modifier is added to the $CO_2$ mobile phase in a gradient of about 50% to 0% (v/v $CO_2$) (or any descending percentage value within 50% to 0%) in about 2 to 4 min (or any fraction of time within this range) with a hold period at a constant modifier percentage at the beginning, end or anytime during the elution period. In some embodiments, the modifier can be added in gradient of about 70% to 0% or more (v/v $CO_2$), about 50% to 0% or more (v/v $CO_2$), or about 30% to 0% or more (v/v $CO_2$). In an embodiment, the modifier is added to $CO_2$ with a gradient of 0% to about 25% in 2.5 min. and a hold at 25% for 1 minute.

In some embodiments, depending on the column dimension chosen and optimization necessary, the flow rate of the mobile phase is set between about 0.1 mL/min to 4 mL/min during the elution period. In an embodiment, the mobile phase flow rate increases in a gradient of about 0.5 mL/min to 4.0 mL/min, or any intervals therebetween. In another embodiment, the mobile phase flow rate decreases in a gradient of 4.0 mL/min to 0.5 mL/min, or any intervals therebetween. In another embodiment, the flow rate remains constant at, for example, about 0.8 mL/min or about 2 mL/min or about 3.5 mL/min.

In some embodiments, depending on the nature of the PAH, the mobile phase further includes one or more additives for optimizing the separation. In an embodiment, one or more additives including, e.g. formic acid, ammonium acetate, isopropyl amine, diethiy amine, ammonium hydroxide or the like, are added to the mobile phase at a concentration range of about 0.5% to 5% (v/v to modifier) or any specific percentage within this range. In an embodiment, the additive is added at a constant amount of 3% (v/v modifier) over the elution period.

In another embodiment, depending on the polarity of the PAH, the gradient duration (tg) of the mobile phase is varied between about 0.1 min to 12 min or any specific period within this range. In an embodiment, tg is about 1 min, or about 2 min, or about 3 min, or about 5 min, or about 7 min. In some embodiments, the entire elution period is less than or equal to about 12 min, or less or equal to than about 8 min, or less than or equal to about 5 min, or less than or equal to about 4 min, or less than or equal to about 3 min, or less than or equal to about 2 min, or less than or equal to about 1.5 min. In some embodiments, the entire elution period is between about 1 min to about 5 min, or any value or range therebetween.

Due to the reason that supercritical and/or liquid $CO_2$ is miscible with the entire eluotropic series, various polar and non-polar modifiers can be added to $CO_2$ to facilitate desorption of a wide variety of analytes. A related advantage of the $CO_2$-based system of the subject technology is its compatibility with a wide range of sample solutions and solvents. Since liquid $CO_2$ is miscible with a wide range of solvents, a sample containing PAHs is not subject to a solvent exchange step prior analysis by the method of subject technology.

In some embodiments, suitable detection methods for detecting the solutes, include, but not limited to, UV, PDA, Evaporative Light Scattering (ELS), CD, FID and Mass Spectroscopy (MS).

Sample Preparation

A sample for analysis can be any sample from biological or non-biological sources that may contain PAHs. For example, a sample can be blood; plasma; urine; cerebrospinal fluid; synovial fluid or other biological fluids; a tissue biopsy; ground water; surface water; drinking water; an aqueous or organic extract of an environmental sample such as a soil sample; a food substance such as a fruit or vegetable juice or milk or an aqueous or aqueous/organic extract of a food substance; a natural product extract from plants; a dye; a pesticide; a preservative; a cleaning agent; an extract of packaging materials or medical devices that come in contact with food, drugs, or the human body A sample can be treated to remove components that could interfere with the detection techniques such as a mass spectrometry technique. A variety of extraction and purification techniques known to those having skill in the art can be used based on the sample type. Solid samples can be grinded and extracted to free the analytes of interest from interfering components. In such cases, a sample can be centrifuged, filtered, and/or subjected to chromatographic techniques to remove interfering components (e.g., cells or tissue fragments). In yet other cases, reagents known to precipitate or bind the interfering components can be added.

In some embodiments, following a sample preparation step (e.g., purification, extraction), the sample is dissolved in a diluent containing at least about 60% organic solvent or at least about 70% organic solvent, or at least about 80% organic solvent, or at least about 90% organic solvent. In other embodiments, following a sample preparation step, the sample includes a polar or non-polar organic solvent, a mixture of organic solvents, or a mixture of water or an aqueous solution and a water-miscible polar organic solvent, e.g., methanol, ethanol, isopropanol, tetrahydrofuran, dichlormethane, hexane, N,N-dimethylformamide, dimethylsulfoxide, acetonitrile or a combination thereof. In an embodiment, the solution is an acidic, basic or neutral aqueous containing, e.g., between about 1% and about 99% water by volume. In another embodiment, the sample solution is an acidic, basic or neutral aqueous containing, e.g., between about 1% and about 75% water by volume. In another embodiment, the sample solution comprises a non-polar organic solvent such as, for example, hexane. The sample solution comprising the analyte can, optionally, further contain one or more additional solutes. In one embodiment, the sample solution is an aqueous solution which includes a complex variety of analytes and solutes. Solutions of this type include, e.g., blood, plasma, urine, cerebrospinal fluid, synovial fluid and other biological fluids, including, e.g., extracts of tissues, such as liver tissue, muscle tissue, brain tissue or heart tissue. Such extracts can be, e.g., aqueous extracts or organic extracts which have been dried and subsequently reconstituted in water or in a water/organic mixture. Sample solutions also include, e.g., ground water, surface water, drinking water or an aqueous or organic extract of an environmental sample, such as a soil sample. Other examples of sample solutions include a food substance, such as a fruit or vegetable juice or milk or an aqueous or aqueous/organic extract of a food substance, such as fruit, vegetable, cereal or meat. Other examples of sample solutions include, e.g., natural products extractions from plants and broths. Other examples of sample solutions include, e.g., dyes, pesticides, preservatives, cleaning agents, or extracts of packaging materials or extracts of medical devices that come in contact with food, drugs, or the human body. Such extracts can be, e.g., aqueous extracts or organic extracts which have been dried and subsequently reconstituted in water or in a water/organic mixture. Such extracts can also be, e.g., aqueous extracts or organic extracts which have not been dried or subsequently reconstituted in water or in another solvent. The solution can be contacted with the porous material in any fashion which allows sorption of the solute to the porous material, such as a batch or chromatographic process. In some embodiments, no derivatization step of the solutes is necessary as the $CO_2$-based system of the subject technology is compatible with a wide range of sample solutions.

In one embodiment, the extracted or purified sample which may include an aqueous or organic solvent or diluent is dried and subsequently reconstituted in a solvent (e.g., water or water/organic mixture) that is compatible with the mobile phase of the method and system of the subject technology. This is known as a solvent exchange step. For example, the extracted or purified sample is dried and then reconstituted in methanol or in methanol and water.

In another embodiment, the extracted or purified sample which is dissolved in an aqueous or organic solvent or in a diluent with at least 60% organic solvent will not undergo solvent exchange or will not be subject to a solvent exchange step before being analyzed by the method and/or system of the subject technology. The absence of a solvent exchange step shortens the analysis period and improves the run time of the method of subject technology.

In some embodiments, sample is prepared with or extracted in an organic solvent wherein the prepared sample is analyzed by the method of the subject technology without additional sample derivatization or solvent exchange (i.e., drying of the solvent and reconstituting the analytes or solutes with a different solvent). The absence of a derivatization step shortens the analysis period and improves the run time of the method of subject technology. In certain embodiments, the analytes are derivatized before analysis by the method and/or system of the subject technology. Various methods for derivatizing analytes are known in the art. In general derivatization fall into three general reaction types: (1) Alkylation of which the general process is esterification, (2) Acylation and (3) Silylation. Common derivatization reagents for the Alkylation type of reactions are Dialkylacetals, Diazoalkales, Pentafluorobenzyl bromide (PFBBr), Benzylbromide, Boron trifluoride (BF3) in methanol or butanol and Tetrabutylammonium hydroxide (TBH) among others. Reagents used for the silylation derivatization process include Hexamethyldisilzane (HMDS), Trimethylchlorosilane (TMCS), Trimethylsilylimidazole (TMSI), Bistrimethylsilylacetamide (BSA), Bistrimethylsilyltrifluoroacetamide (BSTFA), N-methyltrimethylsilyltrifluoroacetamide (MSTFA), Trimethylsilyidiethylamine (TMS-DEA), Nmethyl-N-t-butyldimethylsilyltrifluoroacetamide (MTBSTFA), and Halo-methylsilyl derivatization reagents. Common reagents for the Alkylation process are Fluoracylimidazoles, Fluorinated Anhydrides, N-Methyl-bis(trifluoroacetamide) (MBTFA), Pentafluorobenzoyl Chloride (PFBCl) and hentafluoropropanol (PFPOH).

In certain embodiments, an internal standard can be added to a sample prior to sample preparation. Internal standards can be useful to monitor extraction/purification efficiency. An internal standard can be added to a sample and allowed to equilibrate for a period of time, e.g., 5, 10, 15, 20, 25, 30, 60, 120 or more minutes. Equilibration temperature can be from about 10° C. to about 45° C., or any value in between (e.g., 15, 25, 30, 35, 37, 42, or 44° C.). In certain cases, equilibration can be at room temperature for about 15 minutes.

An internal standard can be any compound that would be expected to behave under the sample preparation conditions in a manner similar to that of one or more of the analytes of interest. For example, a stable-isotope-labeled version of an analyte of interest can be used, such as a deuterated version of an analyte of interest. While not being bound by any theory, the physicochemical behavior of such stable-isotope-labeled compounds with respect to sample preparation and signal generation would be expected to be identical to that of the unlabeled analyte, but clearly differentiable by mass on a mass spectrometer.

To improve the run time and minimize hands-on sample preparation, on-line extraction and/or analytical chromatography of a sample can be used. For example, in certain methods, a sample, such as a urine or blood sample can be extracted using an extraction column, followed by elution onto an analytical chromatography column. The columns can be useful to remove interfering components as well as reagents used in earlier sample preparation steps (e.g., to remove reagents such as acetonitrile). Systems can be coordinated to allow the extraction column to be running while an analytical column is being flushed and/or equilibrated with solvent mobile phase, and vice-versa, thus improving efficiency and run-time. A variety of extraction and analytical columns with appropriate solvent mobile phases and gradients can be chosen by those having ordinary skill in the art.

Various extraction methods are known in the art that can be used to prepare a sample before it being analyzed by the subject technology. Such extraction methods include, but are not limited to, sonication, soxhlet extraction, microwave assisted extraction (MAE), supercritical fluid extraction (SFE), accelerated solvent extraction (ASE), pressurized liquid extraction (PLE), pressurized hot water extraction (PHWE) and/or surfactant assisted extraction (PHWE) in common solvents such as methanol, ethanol, mixtures of alcohols and water, or organic solvents such as ethyl acetate or hexane.

In some embodiments, the concentration of the PAHs in the sample solution is about 5 mg/mL, 4, mg/mL, 2 mg/mL, 1 mg/mL, 0.5 mg/mL, 0.1 mg/mL, 0.05 mg/mL, 0.01 mg/mL, 0.005 mg/mL, 0.001 mg/mL, 0.0001 mg/mL, $1\times10^{-5}$ mg/mL, $1\times10^{-6}$ mg/mL or less. In an embodiment, the concentration of the PAHs in the sample solution being analyzed by the method and system of the subject technology is in ng/mL or pg/mL range or lower. In another embodiment, the sample injection volume for injection into the $CO_2$ based system of the subject technology is about 10 µL, 8 µL, 6 µL, 5 µL, 4 µL, 3 µL, 2 µL, 1 µL.

Detection

In some embodiments, suitable detection methods for detecting the analytes include, but not limited to, UV, photodiode array (PDA), Evaporative Light Scattering (ELS), CD, FID, and Mass Spectrometry (MS).

Depending on the sample that is being analyzed by the method and system of the subject technology, a suitable detector may be used. Suitable detectors are known in the art. For example, if the sample is contains an abundance of analytes (i.e., about 1-10 ppm range or 1 to 10 μg/mL), a detection method such as UV, PDA or ELS may be used. If the sample contains a minute amount of analytes (in ng/mL or pg/mL range), a detection method such as Mass Spectrometry may be used.

Kits

One embodiment of the subject technology features a kit for performing the method of the subject technology. As used herein, the term kit refers to a collection of parts and reagents bundled together with suitable packaging and instructions for their use. One kit for performing an analysis of a sample for the analytical levels or the presence or absence of PAHs, in accordance with the subject technology includes internal standards for calibrating and facilitating the identification of one or more PAHs; sample preparation devices or reagents and materials for performing sample purification, extraction, preparation or derivatization; and a chromatography column for separating or detecting PAHs of the sample.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

This subject technology is further illustrated by the following examples which should not be construed as limiting. The contents of all references, patents and published patent applications cited throughout this application, are incorporated herein by reference.

EXAMPLES

Example 1

Rapid Separation and Analysis of Sixteen Different PAHs

Mobile Phase=$CO_2$ with Methanol as Modifier

A working sample of sixteen PAHs listed in Table 2 (below) was prepared by diluting a mixture of these compounds in 9:1 acetonitrile:methanol solution.

TABLE 2 a list of sixteen PAHs considered by the EPA as toxic

| Compound | Formula | Mol wt | Structure |
|---|---|---|---|
| Naphthalene | $C_{10}H_8$ | 128.17 | 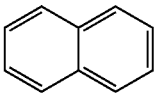 |
| Acenaphthylene | $C_{12}H_8$ | 152.2 | 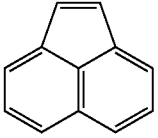 |
| Acenaphthene | $C_2H_{10}$ | 154.2 | 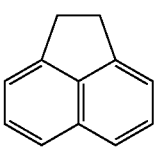 |
| Fluorene | $C_{13}H_{10}$ | 166.2 | 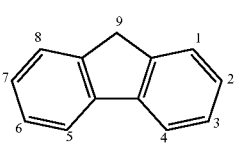 |
| Anthracene | $C_{14}H_{10}$ | 178.2 | 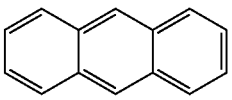 [SMILES: c1ccc2cc3ccccc3cc2c1] |
| Phenanthrene | $C_{14}H_{10}$ | 178.2 | 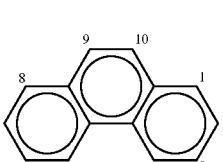 |
| Fluoroanthene | $C_{16}H_{10}$ | 202.2 | 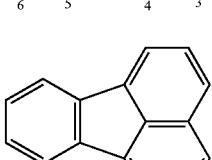 |
| Pyrene | $C_{16}H_{10}$ | 202.2 | 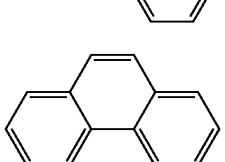 |
| Benz[a]anthracene | $C_{18}H_{12}$ | 228.2 | 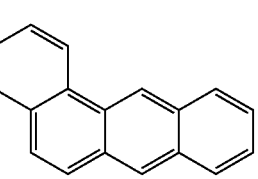 |
| Chrysene | $C_{18}H_{12}$ | 228.2 | 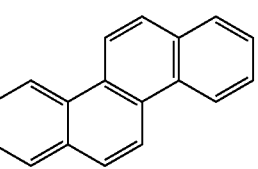 |

TABLE 2-continued a list of sixteen PAHs considered by the EPA as toxic

| Compound | Formula | Mol wt | Structure |
|---|---|---|---|
| Benzo[b] fluoranthene | $C_{20}H_{12}$ | 252.3 | 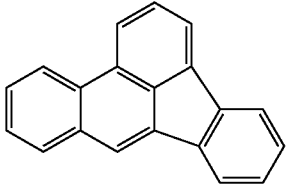 [SMILES: c1ccc2c(c1)-c1cccc3c1c-2cc1ccccc13] |
| Benzo[k] fluoranthene | $C_{20}H_{12}$ | 252.3 | 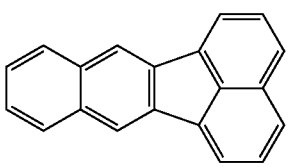 [SMILES: c1ccc2cc3c(cc2c1)-c1cccc2cccc-3c12] |
| Benzo[a]pyrene | $C_{20}H_{12}$ | 252.3 | 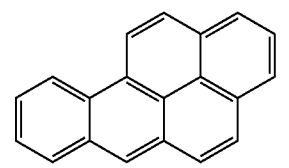 [SMILES: c1ccc2c(c1)cc1ccc3cccc4ccc2c1c34] |
| Benzo[ghi] perylene | $C_{22}H_{12}$ | 276.3 | 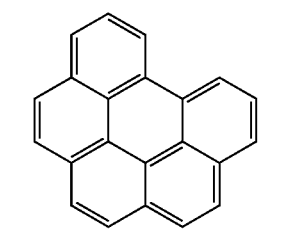 [SMILES: c1cc2ccc3ccc4ccc5cccc6c(c1)c2c3c4c56] |
| Indeno[1,2,3-cd]pyrene | $C_{22}H_{12}$ | 276.3 | 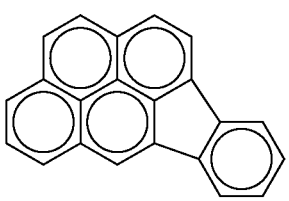 |
| Dibenz[a,h] anthracene | $C_{22}H_{14}$ | 278.3 | 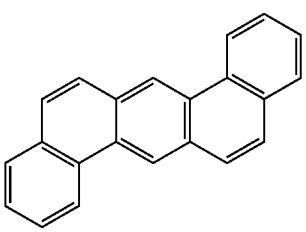 [SMILES: c1ccc2c(c1)ccc1cc3c(ccc4ccccc43)cc12] |

The sample was applied to a chromatography column which included a solid phase stationary phase column with particles having polar/non-polar surface characteristics (i.e., ACQUITY UPC² HSS C18 SB (1.7 μm, 3.0 mm×100 mm) column, Waters Corp., Milford, Mass.) in a $CO_2$-based chromatography system (i.e., ACQUITY Ultra Performance Convergence Chromatography (UPC2)®, Waters Corp., Milford, Mass.) having a photo-diode array detector with a 3D channel scanning in the range of 210-400 nm and 2D channel acquiring at 254 nm with a sampling rate of 20 points/sec. The mobile phase in this system was $CO_2$ with methanol was added to the $CO_2$ mobile phase in a gradient of 0% to 25% (v/v $CO_2$) in 2.5 minutes with 1 minute hold at 25%. The flow rate of the mobile phase was 2 mL/min. The CCM system pressure was 1800 psi. The column temperature was 50° C. The injection volume as 2 μL. The total instrument run time was 4 min.

The results obtained in this example demonstrated that the column chemistry used in this example facilitated a rapid analysis of PAHs in less than about 3 minutes. See FIG. 4. The peak numbers in FIG. 4 correspond to the PAHs listed in Table 3 below:

TABLE 3

Figure 4:
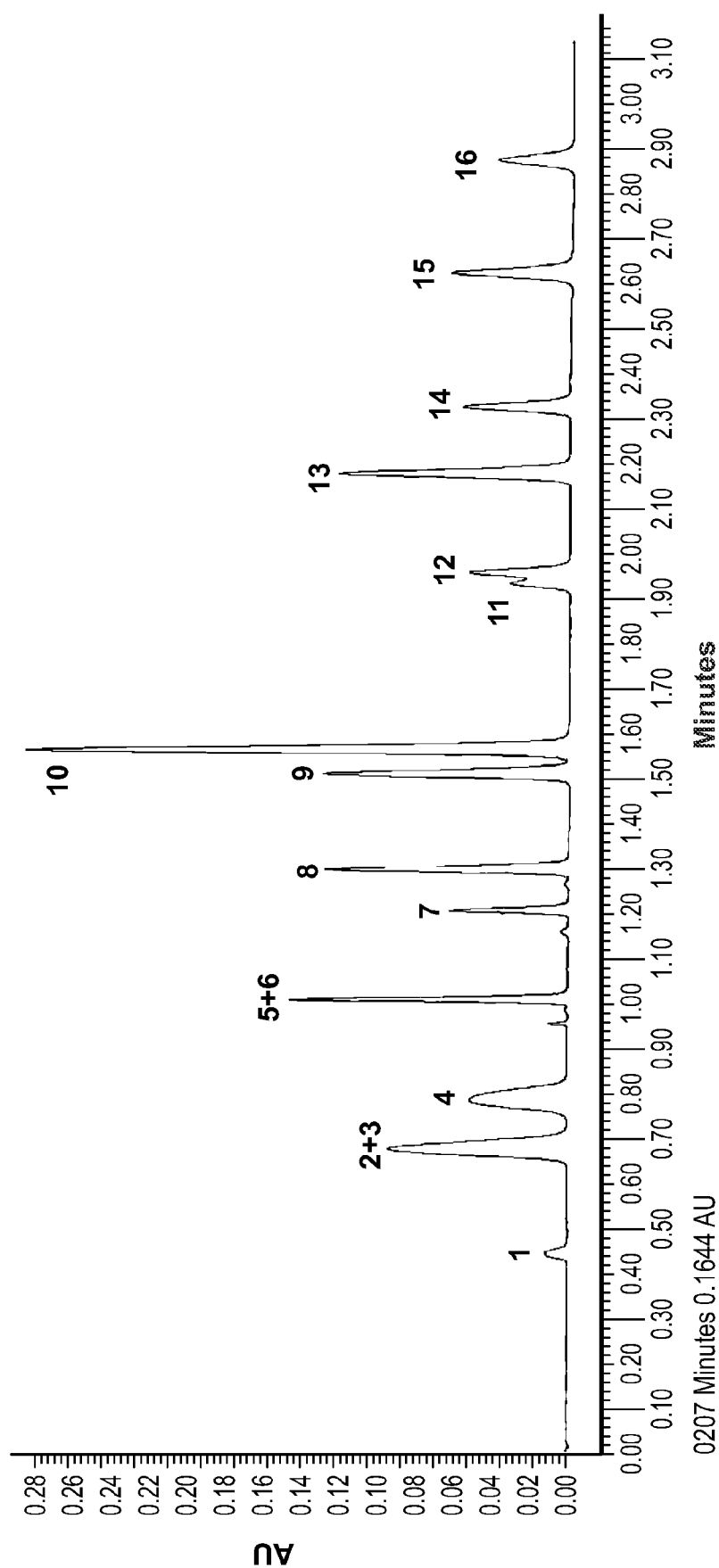
FIG. 4 is a chromatographic analysis of a mixture of sixteen PAHs listed in Table 2, according to the $CO_2$-based system and method of the subject technology. In generating the chromatogram shown in this figure, the system included an HSS C18, 3.0 mm×100 mm, 1.7 µm column (Waters Corp., Milford, Mass.). A mixture of $CO_2$ and methanol was used as the mobile phase for eluting the PAHs. For eluting PAHs, the modifier, i.e., methanol, was added to $CO_2$ in a gradient of 0 to 25% in 2.5 min. and held at 25% for 1 min. Peaks were detected using a photo-diode array detector with a 3D channel scanning in the range of 210-400 nm and 2D channel acquiring at 254 nm with a sampling rate of 20 points/sec. The peak numbers in FIG. 4 correspond to the PAHs listed in Table 3.
Figure 6:
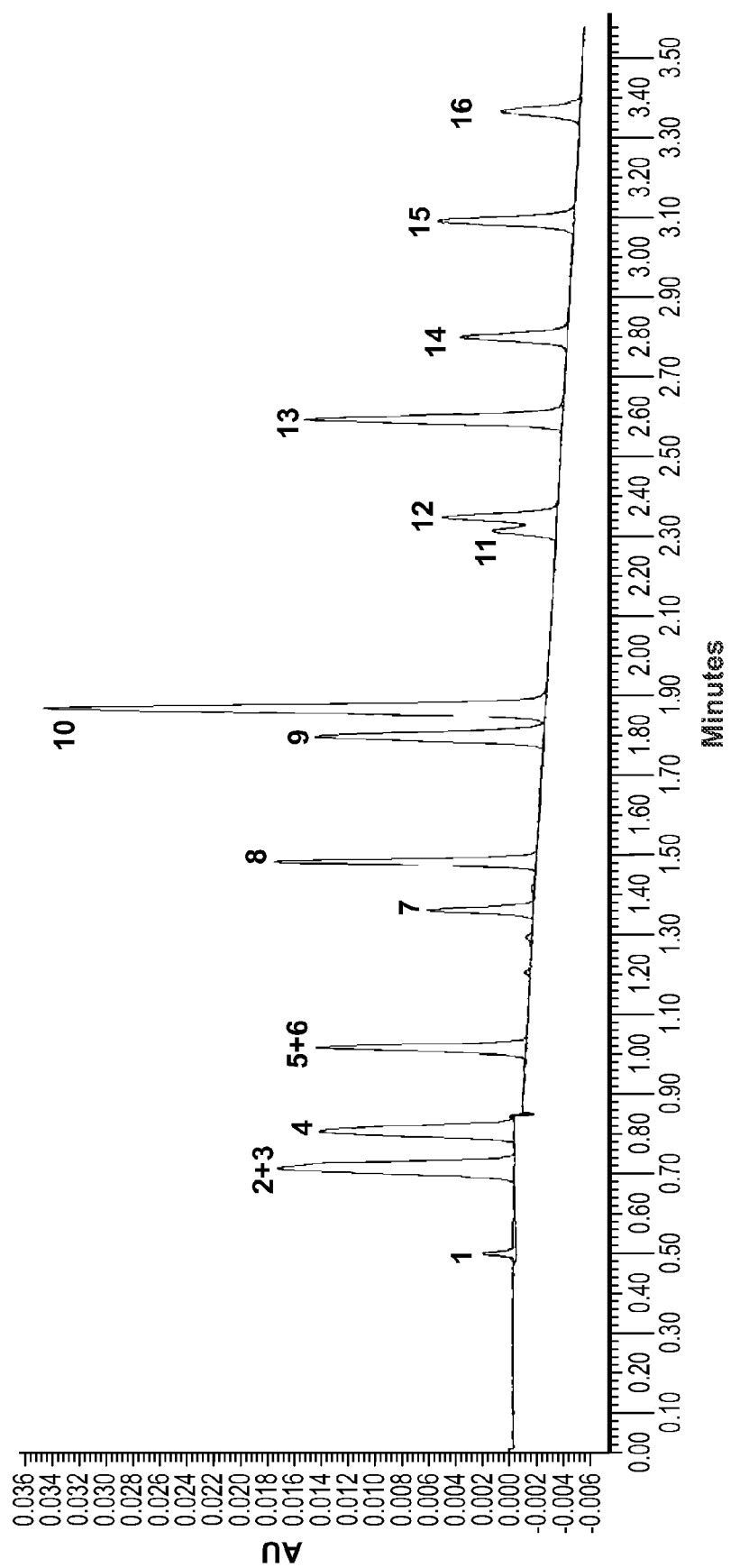
FIG. 6 is a chromatographic analysis of the same sixteen PAHs under the same conditions as described in the FIG. 4 description with the exception that acetonitrile was used as the modifier in placed of methanol. The peak numbers in the figure correspond to the PAHs listed in Table 3.

List of PAHs corresponding to the peaks in FIGS. 4 and 6.

| Peak No. | Compound Name | Retention time (min) |
|---|---|---|
| 1 | Naphthalene | 0.442 |
| 2 | Acenaphthylene | 0.678 |
| 3 | Acenaphthene | 0.678 |
| 4 | Fluorene | 0.787 |
| 5 | Phenanthrene | 1.015 |
| 6 | Anthracene | 1.015 |
| 7 | Fluoranthene | 1.216 |
| 8 | Pyrene | 1.309 |
| 9 | Benzo [a] anthracene | 1.524 |
| 10 | Chrysene | 1.579 |
| 11 | Benzo [b] fluoranthene | 1.948 |
| 12 | Benzo [k] fluoranthene | 1.973 |
| 13 | Benzo [a] pyrene | 2.197 |
| 14 | Dibenzo [ah] anthracene | 2.345 |
| 15 | Benzo [ghi] perylene | 2.647 |
| 16 | Indeno [1,2,3-cd] pyrene | 2.901 |

These results demonstrated that the subject technology provides a rapid simple analytical method for detecting a wide range of PAHs. In addition, these results showed that the column chemistry used in this example facilitated the generation of a chromatogram with high peak resolution and high signal-to-noise ratios, which was unexpected.

Example 2

Reproducibility Test for the Analysis of Sixteen Different PAHs

In this example, the same mixture of sixteen PAHs studied in Example 1 was analyzed repeatedly using the same column chemistry and the $CO_2$-based chromatography system described in Example 1. All parameters were kept the same as in Example 1.

Figure 5:
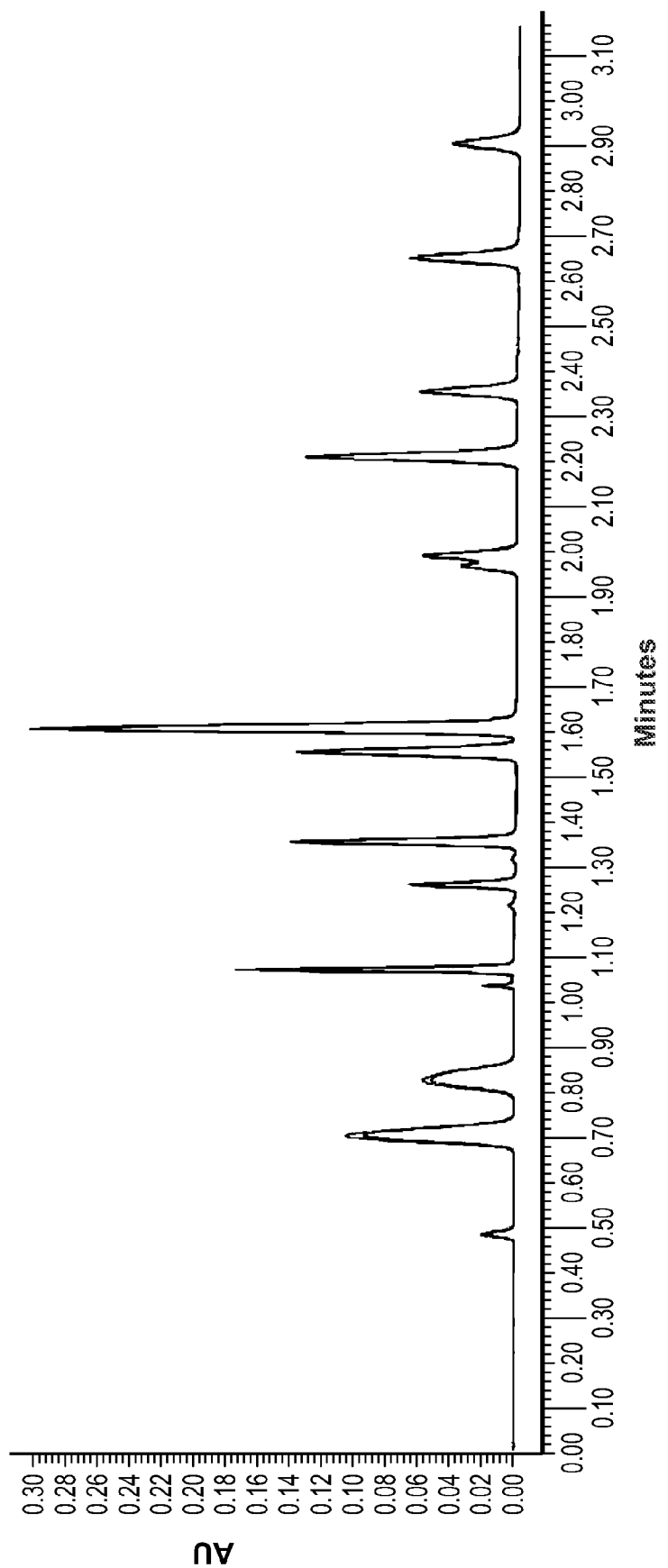
FIG. 5 illustrates the reproducibility of the results obtained by the method and system of the subject technology. In this figure, chromatograms obtained from repeated injections of the PAH sample tested in Example 1 are superimposed on one another to show that little or no variations occurs in the chromatograms obtained at different times. This figure also illustrates the robustness of the $CO_2$-based system and method of the subject technology in analyzing PAHs.

As shown in FIG. 5, different injections still produced reproducible results. This test demonstrated that the method and the $CO_2$-based system of the subject technology were robust in facilitating the generation of rapid and reproducible results each time, which was surprisingly and unexpected.

Example 3

Rapid Separation and Analysis of Sixteen Different PAHs

Mobile Phase=$CO_2$ with Acetonitrile as Modifier

In this example, the same mixture of sixteen PAHs studied in Example 1 was analyzed according to the method of the subject technology in which the mobile phase was $CO_2$. The column chemistry was the same as in Example which included hybrid particles with polar/non-polar surface characteristics (i.e., ACQUITY UPC² HSS C18 SB (1.7 μm, 3.0 mm×100 mm) column, Waters Corp., Milford, Mass.). All other parameters were kept the same as in Example 1 except the modifier, which was acetonitrile for this example. Accordingly, for eluting the PAH analytes, acetonitrile was added to the $CO_2$ mobile phase at a gradient of 0% to 25% (v/v $CO_2$) in 2.5 minutes and a one-minute hold at 25%. The data obtained in this example showed that the change in modifier, from methanol to acetonitrile, did not significantly affect the profile of the peaks although a slight retention shift was seen. This data showed that the column chemistry used in this example could still facilitate the analysis of PAHs in a less than about 3.4 minutes and produce a chromatogram with high resolution and minimum noise, which was unexpected. See FIG. 6.

Example 4

Rapid Separation and Analysis of Eighteen Different PAHs

Mobile Phase=$CO_2$ with Acetonitrile as Modifier

A working sample of eighteen PAHs listed in Table 4 (below) was prepared by diluting a mixture of these compounds in a 9:1 acetonitrile:methanol solution.

TABLE 4 a list of eighteen PAHs considered by the EPA as toxic

| Compound | Formula | Mol wt | Structure |
|---|---|---|---|
| Naphthalene | $C_{10}H_8$ | 128.17 | 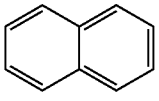 |
| 1-methyl naphthalene | $C_{11}H_{10}$ | 142.2 | 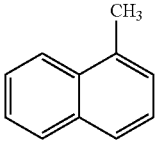 |
| 2-methyl naphthalene | $C_{11}H_{10}$ | 142.2 | 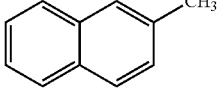 |
| Acenaphthylene | $C_{12}H_8$ | 152.2 | 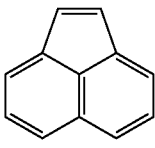 |
| Acenaphthene | $C_2H_{10}$ | 154.2 | 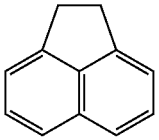 [SMILES: c1cc2c3c(cccc3c1)CC2] |
| Fluorene | $C_{13}H_{10}$ | 166.2 | 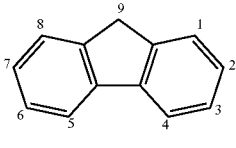 |
| Anthracene | $C_{14}H_{10}$ | 178.2 | 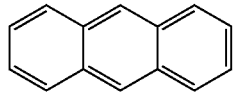 [SMILES: c1ccc2cc3ccccc3cc2c1] |

TABLE 4-continued a list of eighteen PAHs considered by the EPA as toxic

| Compound | Formula | Mol wt | Structure |
|---|---|---|---|
| Phenanthrene | $C_{14}H_{10}$ | 178.2 | 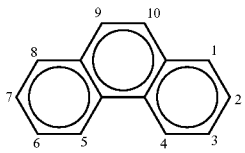 |
| Fluoroanthene | $C_{16}H_{10}$ | 202.2 | 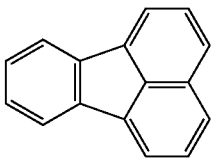 [SMILES: c1ccc2c(c1)-c1cccc3cccc-2c13] |
| Pyrene | $C_{16}H_{10}$ | 202.2 | 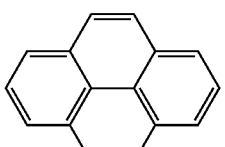 |
| Benz[a]anthracene | $C_{18}H_{12}$ | 228.2 | 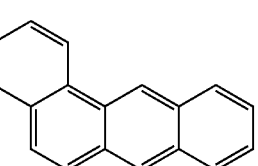 |
| Chrysene | $C_{18}H_{12}$ | 228.2 | 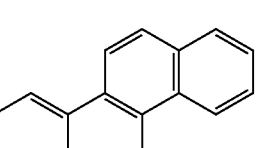 |
| Benzo[b]fluoranthene | $C_{20}H_{12}$ | 252.3 | 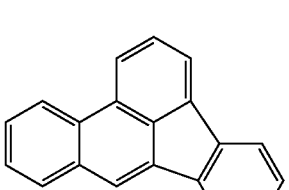 |
| Benzo[k]fluoranthene | $C_{20}H_{12}$ | 252.3 | 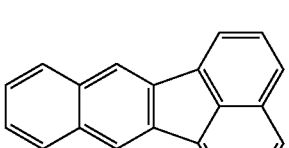 |
| Benzo[a]pyrene | $C_{20}H_{12}$ | 252.3 | 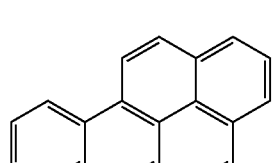 |

TABLE 4-continued a list of eighteen PAHs considered by the EPA as toxic

| Compound | Formula | Mol wt | Structure |
|---|---|---|---|
| Benzo[ghi] perylene | $C_{22}H_{12}$ | 276.3 | 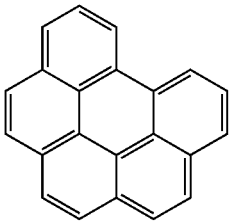 [SMILES: c1cc2ccc3ccc4ccc5cccc6c(c1)c2c3c4c56] |
| Indeno[1,2,3-cd]pyrene | $C_{22}H_{12}$ | 276.3 | 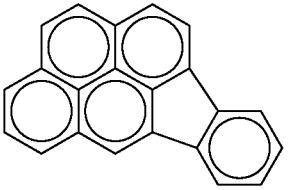 |
| Dibenz[a,h] anthracene | $C_{22}H_{14}$ | 278.3 | 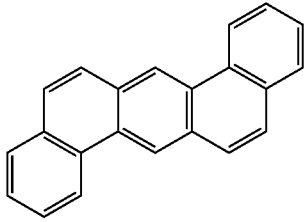 [SMILES: c1ccc2c(c1)ccc1cc3c(ccc4ccccc43)cc12] |

The sample was injected into the $CO_2$-based chromatography system of the subject technology which included a chromatography column with particles having polar/non-polar characteristics (i.e. ACQUITY UPC² HSS C18 SB (1.7 μm, 3.0 mm×150 mm) column, Waters Corp., Milford, Mass.) and a photo-diode array detector with a 3D channel scanning in the range of 210-400 nm and 2D channel acquiring at 254 nm with a sampling rate of 20 points/sec. The mobile phase in this system was liquid $CO_2$ with a modifier, acetonitrile, being added to the $CO_2$ mobile phase in a gradient of 0% to 25% (v/v $CO_2$) in 3.5 minutes and hold at 25% for 1 min. The flow rate was 2 mL/min. The CCM back pressure was 1800 psi. The column temperature was 50° C. The injection volume was 2 μL. The total instrument run time was 4 min.

The chromatogram generated in this example showed the separation of the eighteen PAHs in about 4.2 minutes with peaks well-resolved with high signal-to-noise ratios. See FIG. 7. The peak numbers in FIG. 7 correspond to the PAHs listed in Table 5 below:

TABLE 5

Figure 7:
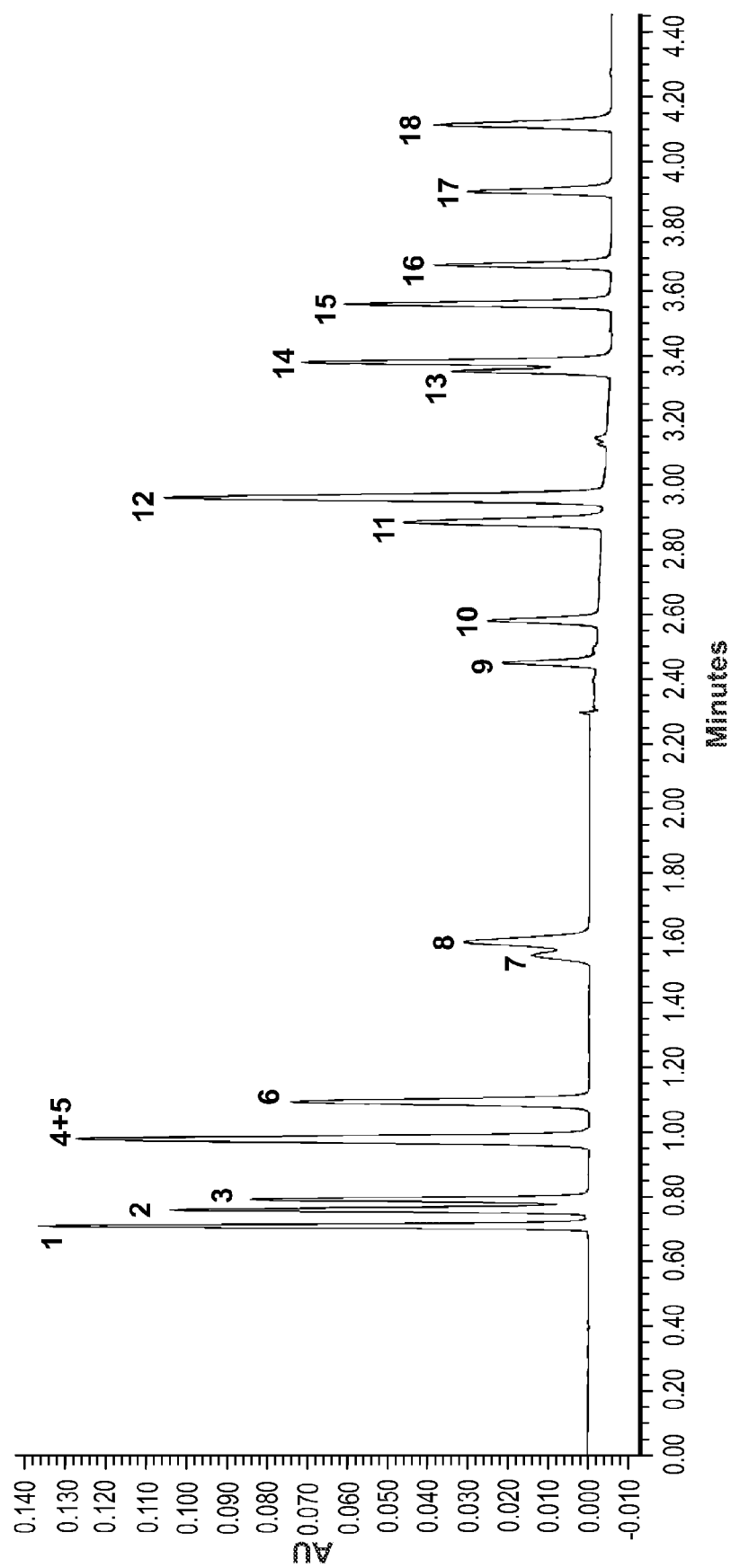
FIG. 7 is a chromatographic analysis of a mixture of eighteen PAHs listed in Table 4 using the $CO_2$-based system and method of the subject technology. For generating this chromatogram, the $CO_2$-based system of the subject technology included an HSS C18, 3.0 mm×150 mm, 1.7 μm, column (Waters Corp., Milford, Mass.). The mobile phase used for eluting the PAHs was a mixture of liquid $CO_2$ and acetonitrile, as the modifier. The modifier was injected into $CO_2$ in a gradient of 0 to 25% in 3.5 min, and held at 25% for 1 min. The peaks were detected by a photo-diode array detector with a 3D channel scanning in the range of 210-400 nm and 2D channel acquiring at 254 nm with a sampling rate of 20 points/sec. The peak numbers in the figure correspond to the PAHs listed in Table 5.

List of PAHs corresponding to the peaks in FIG. 7.

| Peak No. | Compound Name | Retention time (min) |
|---|---|---|
| 1 | Naphthalene | 0.71 |
| 2 | 1-methyl naphthalene | 0.76 |
| 3 | 2-methyl naphthalene | 0.792 |
| 4 | Acenaphthylene | 0.98 |
| 5 | Acenaphthene | 0.98 |
| 6 | Fluorene | 1.095 |
| 7 | Anthracene | 1.548 |
| 8 | Phenanthrene | 1.591 |
| 9 | Fluoranthene | 2.453 |
| 10 | Pyrene | 2.582 |
| 11 | Benzo (a) anthracene | 2.888 |
| 12 | Chrysene | 2.964 |
| 13 | Benzo (b) fluoranthene | 3.356 |
| 14 | Benzo (k) fluoranthene | 3.383 |
| 15 | Benzo (a) pyrene | 3.563 |
| 16 | Dibenzo (a, h) anthracene | 3.683 |
| 17 | Benzo (g, h, i) perylene | 3.913 |
| 18 | Indeno (1,2,3-cd) pyrene | 4.119 |

These results demonstrated that PAHs can rapidly and accurately be analyzed according to the method of the subject technology. In particular, these results showed that a chromatography column with particles having non-polar or polar/non-polar surface characteristics are capable of facilitating rapid and accurate analysis of PAHs in a $CO_2$-based chromatography system.

Example 5

Rapid Separation and Analysis of Eighteen Different PAHs

Mobile Phase=$CO_2$ with Acetonitrile as Modifer

In this example, the same mixture of eighteen PAHs studied in Example 4 was analyzed by the $CO_2$-based system of the subject technology. In this example, the sample was applied to the $CO_2$-based chromatography system of the subject technology with a chromatography column containing solid stationary phase particles having polar surface characteristics (i.e., CSH Fluoro-phenyl (1.7 μm, 3.0 mm×100 mm) column, Waters Corp., Milford, Mass.). The mobile phase in this system was liquid $CO_2$ with a modifier, acetonitrile, being added to the $CO_2$ mobile phase in a gradient of 0% to 15% (v/v $CO_2$) in 4.5 minutes. The flow rate was 2 mL/min. The CCM back pressure was 1800 psi. The column temperature was 50° C. The injection volume was 2 μL. The total instrument run time was 5 min. For detection, a photo-diode array detector with a 3D channel scanning in the range of 210-400 nm and 2D channel acquiring at 254 nm with a sampling rate of 20 points/sec was used.

Figure 8:
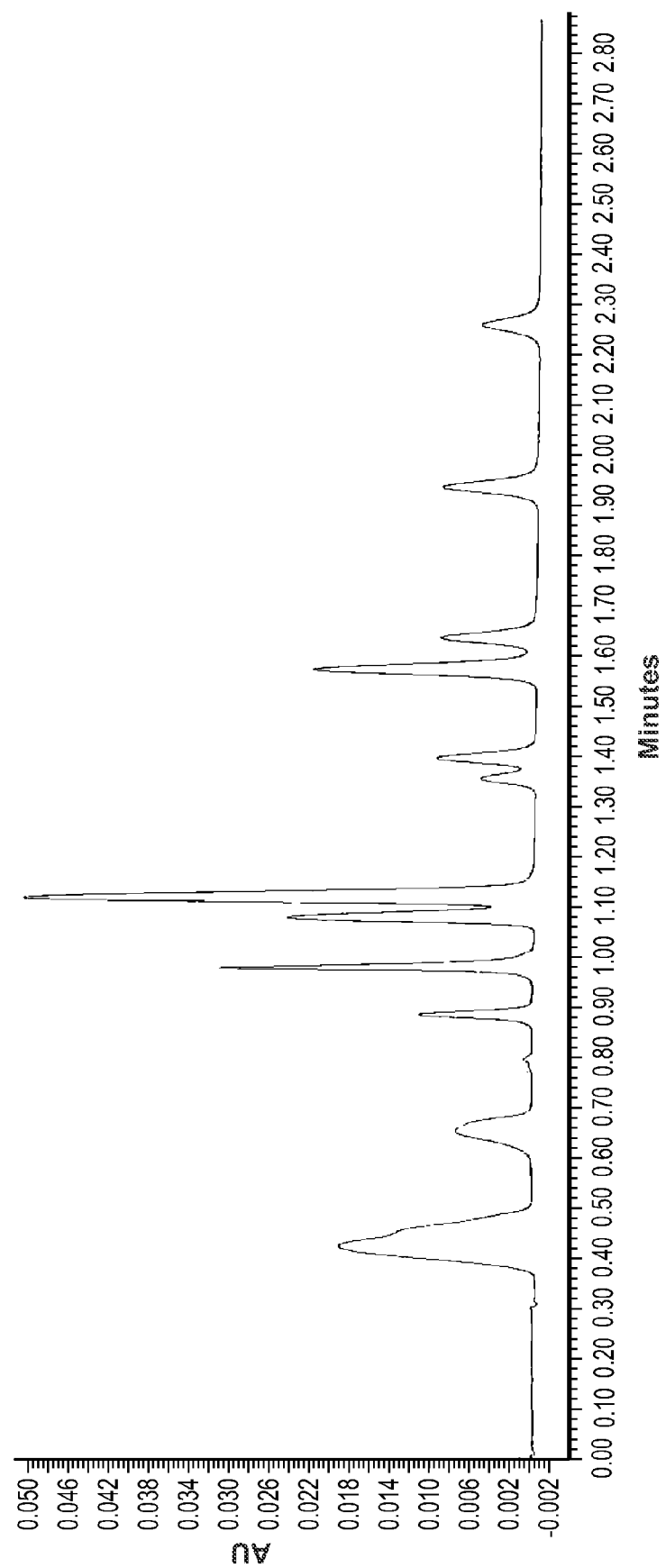
FIG. 8 is a chromatogram obtained from a chromatographic analysis of the eighteen PAHs listed in Table 4, according to the $CO_2$-based system and method of the subject technology. For generating this chromatogram, a CSH Fluoro-phenyl, 3.0 mm×100 mm, 1.7 μm, column (Waters Corp., Milford, Mass.) was used. The mobile phase for eluting the PAHs was a mixture of $CO_2$ and acetonitrile. The modifier, i.e., acetonitrile, was injected into $CO_2$ in a gradient of 0 to 15% in 4.5 min. The peaks were detected using a photo-diode array detector with a 3D channel scanning in the range of 210-400 nm and 2D channel acquiring at 254 nm with a sampling rate of 20 points/sec.

The chromatogram obtained in this example showed that a number of the analytes were co-eluted. See FIG. 8. Although co-elution occurred for a number of PAHs because of the polar surface characteristics of the particles used in the solid stationary phase in this example, the results unexpectedly showed that separating PAHs in less than about 5 minutes and observing well-resolved peaks with high signal-to-noise ratios were still possible. Thus, it was concluded that although particles having polar surface characteristics may not be ideal for facilitating the analysis of PAHs when a PDA detector is used in conjunction with a $CO_2$-hatted system, such stationary phase particles are still capable of facilitating a rapid and efficient analysis of PAHs when a different detector such as a mass spectrometer is used in tandem with the $CO_2$-based system.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The

What is claimed is:

1. A method for detecting one or more polycyclic aromatic hydrocarbons (PAHs) in a sample by means of a $CO_2$-based chromatography analysis comprising:
   providing a sample comprising one or more PAHs for analysis; wherein the sample is prepared with, extracted or dissolved in a diluent comprising at least 60% organic solvent, with the proviso that the sample is analyzed without a solvent exchange step;
   applying the sample to a chromatography column with a solid stationary phase comprising inorganic or hybrid particles having a mean particle size of about 0.5 to about 3.5 microns, wherein said particles have a non-polar or polar/non-polar surface functionality, and wherein the particles retain said one or more PAHs;
   eluting the one or more PAHs from the chromatography column by a mobile phase comprising a mixture of liquid $CO_2$ and a modifier to form one or more eluted PAHs; wherein the mobile phase has a pre-column dwell volume of about 75 µL to about 500 µL; and
   detecting said one or more eluted PAHs.

2. The method of claim 1, wherein the sample is not subject to a derivatization step.

3. The method of claim 2, wherein the organic portion of the hybrid particles comprises substituted or unsubstituted $C_1$-$C_{18}$ alkylene, alkenylene, alkynylene or arylene moiety bridging two or more atoms of the inorganic portion.

4. The method of claim 1, wherein the particles having a non-polar surface functionality comprise capped particles with non-polar surface modifiers comprising an alkyl group, alkenyl group, alkynyl group, aryl group, an alkyl or aryl group containing one or more embedded non-polar functionalities, or a mixture thereof.

5. The method of claim 1, wherein the particles having a polar/non-polar surface functionality comprise uncapped particles with free surface hydroxyl groups and non-polar surface modifiers comprising an alkyl group, alkenyl group, alkynyl group, aryl group, an alkyl or aryl group containing one or more embedded non-polar functionalities, or a mixture thereof.

6. The method of claim 1, wherein the particles have a mean particle size of about 0.5 to about 2 microns.

7. The method of claim 1, wherein the particles have a mean pore volume in the range of about 0.1 to about 2.5 cm/g.

8. The method of claim 1, wherein the particles have a mean pore diameter in the range of about 100 to about 1000 Angstroms.

9. The method of claim 1, wherein the inorganic particles comprise aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof.

10. The method of claim 1, wherein the hybrid particles comprise an inorganic portion and an organic portion.

11. The method of claim 10, wherein the inorganic portion of the hybrid particles comprises silicone, aluminum, titanium, cerium, zirconium, barium, cobalt, copper, europium, gadolinium, iron, nickel, samarium, silver, titanium, diamond, zinc, boron or oxides thereof, silicon carbide, carbon black, carbon nanotubes, ceramic, glass, metallic materials or mixtures thereof.

12. The method of claim 10, wherein the organic portion of the hybrid particles comprises substituted or unsubstituted $C_1$-$C_{18}$ alkane, alkylene, alkenylene, alkynylene or arylene moiety bonded to one or more atoms of the inorganic portion.

13. The method of claim 1, wherein the chromatography column is kept in a temperature range of about 5° C. to about 85° C.

14. The method of claim 1, wherein the mobile phase further comprises a modifier added to the liquid $CO_2$ in a constant or gradient mode or both over an elution period or a fraction thereof.

15. The method of claim 14, wherein the modifier is a polar water-miscible organic solvent selected from the group consisting of methanol, ethanol or isopropanol, acetonitrile, acetone, tetrahydrofuran, mixtures thereof, and mixtures of water and any of these solvents.

16. The method of claim 14, wherein the gradient mode comprises increasing or decreasing flow volume of the modifier.

17. The method of claim 14, wherein the elution period is about 5 minutes.

18. The method of claim 14, wherein the gradient mode comprises increasing the flow volume of the modifier from about 0% to about 50% (v/v $CO_2$) or any intervals therebetween.

19. The method of claim 14, wherein the gradient mode comprises increasing the flow volume of the modifier from about 0% to about 25% (v/v $CO_2$).

20. The method of claim 1, wherein the liquid $CO_2$ is in a supercritical state or a subcritical state or both.

21. The method of claim 1, wherein the detection comprises determining the levels or the presence or absence of the one or more PAHs.

22. The method of claim 1, wherein the detection is by way of a mass spectrometer; Evaporative Light Scattering (ELS) detector, Circular Dichroism (CD) detector, Flame Ionization Detector (FID) or a photodiode array detector (PDA).

23. The method of claim 1, wherein the sample comprises an environmental sample, chemical sample, food sample, biological sample, or an extract thereof.

24. The method of claim 1, wherein the chromatography column is part of a chromatography system comprising a pre-column mobile phase dwell volume of about 100 to about 500 µL; wherein said pre-column mobile phase dwell volume is the volume of the mobile phase present in a fluidic connection between a junction at which the $CO_2$ and the modifier are mixed and the head of the chromatography column.

25. The method of claim 1, wherein the one or more PAHs are eluted from the chromatography column by the mobile phase with a flow rate of about 1 to 4 mL/min.

26. The method of claim 1, wherein the chromatography column has a length of about 50 to 150 mm and an internal diameter about 2 to 4 mm.

27. A chromatography method for detecting one or more polycyclic aromatic hydrocarbons (PAHs) in a sample comprising the steps of:
   providing a sample comprising one or more PAHs for analysis; wherein the sample is prepared with, extracted or dissolved in a diluent comprising at least 60% organic solvent, with the proviso that the sample is analyzed without a solvent exchange step;
   applying the sample to a chromatography column with a solid stationary phase comprising inorganic or hybrid particles having a mean particle size of about 0.5 to about 3.5 microns, wherein said particles have a polar surface functionality, and wherein the particles retain said one or more PAHs;

eluting the one or more PAHs from the chromatography column by a mobile phase comprising a liquid $CO_2$ to form one or more eluted PAHs, wherein the mobile phase has a pre-column dwell volume of about 75 µL to about 500 µL; and detecting said one or more eluted PAHs by a mass spectrometer.

28. A method for detecting one or more PAHs comprising:
(1) providing a sample comprising one or more PAHs for analysis; wherein the sample is prepared with, extracted or dissolved in a diluent comprising at least 60% organic solvent, with the proviso that the sample is not subject to a solvent exchange step;
(2) applying the sample to a chromatography system comprising:
  (a) a column with a solid stationary phase comprising an inorganic or hybrid particle having a mean particle size of about 0.5 to about 3.5 microns, wherein said particle has a non-polar or polar/non-polar surface functionality, wherein said column has a length of about 50 to 150 mm and an internal diameter about 2 to 4 mm, and wherein the solid stationary phase retains said one or more PAHs;
  (b) a pre-column mobile phase dwell volume of about 75 µL to about 500 µL; wherein said pre-column dwell volume comprises a space within a fluidic connection between a junction at which the $CO_2$ and the modifier are mixed to the head of the column; and
  (c) a post-column mobile phase dwell volume of about 10 µL to about 450 µL; wherein said post-column dwell volume comprises a space within a fluidic connection between the end of the column and a detector;
(3) eluting the one or more PAHs from the chromatography column by a mobile phase comprising a mixture of $CO_2$ and a modifier to form one or more eluted PAHs, wherein the mobile phase has a flow rate of about 1 to 4 mL/min; and
(4) detecting said one or more eluted PAHs.

29. A kit for performing analysis or detecting one or more PAHs in a sample comprising:
a sample preparation device for preparing the sample comprising one or more PAHs for analysis; wherein the sample is prepared with, extracted or dissolved in a diluent comprising at least about 60% organic solvent, with the proviso that the sample is analyzed without a solvent exchange step;
a chromatography column with a solid stationary phase comprising inorganic or hybrid particles having a mean particle size of 0.5 to 3.5 microns; wherein said particles have a non-polar or polar/non-polar surface functionality and retain said one or more PAHs; and
one or more standards for calibrating, and facilitating the analysis and detection of the one or more PAHs.

* * * * *